United States Patent [19]

Wrobel et al.

[11] Patent Number: 4,820,727

[45] Date of Patent: Apr. 11, 1989

[54] N-ACYL-N-NAPHTHOYLGLYCINES AS ALDOSE REDUCTASE INHIBITORS

[75] Inventors: Jay E. Wrobel, Lawrenceville; Kazimir Sestanj, Monmouth Junction, both of N.J.

[73] Assignee: American Home Products Corporation, New York, N.Y.

[21] Appl. No.: 137,406

[22] Filed: Dec. 23, 1987

[51] Int. Cl.$^4$ .................. C07C 125/065; A61K 31/27
[52] U.S. Cl. ...................................... 514/510; 560/28
[58] Field of Search ......................... 560/28; 514/510

[56] References Cited

U.S. PATENT DOCUMENTS

| | | | |
|---|---|---|---|
| 4,391,816 | 7/1983 | Sestani | 424/273 |
| 4,391,825 | 7/1983 | Bellini | 560/39 |
| 4,439,617 | 3/1984 | Sestani | 560/39 |
| 4,447,452 | 5/1984 | Sestani | 424/319 |
| 4,568,693 | 2/1986 | Sestani | 514/524 |
| 4,672,058 | 6/1987 | Bellini | 514/62 |
| 4,672,059 | 6/1987 | Sestani | 514/62 |

OTHER PUBLICATIONS

Y. Mitin et al., CA 70: 68721m.
A. Bates et al., Helv. Chim. Acta, 58 (3), 688 (1975).

*Primary Examiner*—Michael L. Shippen
*Attorney, Agent, or Firm*—Walter Patton

[57] ABSTRACT

Disclosed herein are N-acyl-N-naphthoylglycines and methods of their preparation. The N-acyl-N-naphthoylglycines are novel aldose reductase inhibitors useful for the treatment or prevention of diabetic complications.

11 Claims, No Drawings

N-ACYL-N-NAPHTHOYLGLYCINES AS ALDOSE REDUCTASE INHIBITORS

BACKGROUND OF THE INVENTION

This invention relates to N-acyl-N-naphthoylglycines, to the processes for their preparation, to methods for using the compounds, and to pharmaceutical preparations thereof. The compounds have pharmaceutical properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn resulted from the high levels of glucose characteristic of the diabetic patient.

In mammals, including humans, the key enzyme involved in the conversion of hexoses to polyols (e.g. the sorbitol pathway) is aldose reductase. J. H. Kinoshita and collaborators, see J. H. Kinoshita et al, Biochem. Biophys. Acta, 158,472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesireable accumulation of sorbitol has been demonstrated in the lens, peripheral nervous cord and kidney of diabetic animals, see A. Pirie and R. van Heyningen, Exp. Eye Res., 3,124 (1964); L. T. Chylack and J. H. Kinoshita, Invest. Ophthal., 8,401 (1969) and J. D. Ward and R. W. R. Baker, Diabetol., 6,531 (1970).

The closest prior art is K. Sestanj et al, U.S. Pat. No. 4,568,693, 1986, (Example 52) and U.S. Pat. No. 4,439,617, 1984, (Example 60). K. Sestanj et al, disloses N-naphthoylglycine derivatives having aldose reductase activity. The compounds of the present invention differ in that they contain a 2-substituent on the naphthalene ring and the N-methyl group has been replaced by an acyl group. Still other related compounds having a similar utility are N-naphthoylglycine derivatives of Bellini et al, U.S. Pat. No. 4,672,058, 1987, and Sestanj et al, U.S. Pat. No. 4,672,059, 1987; N-(naphthalenylthioxomethyl)amino acid derivatives of K. Sestanj et al, U.S. Pat. No. 4,391,816, 1983; N-[(2-naphthalenyl)thioxomethyl]glycine derivatives of K. Sestanj, U.S. Pat. No. 4,447,452, 1984; and N-[[6-(lower alkoxy)-5-(trifluoromethylthio)-1-naphthalenyl]thioxomethyl]-N-(lower alkyl)-glycines of F. Bellini et al, U.S. Pat. No. 4,391,825, 1983. Accordingly, the present compounds represent an important new approach for the treatment of diabetes mellitus.

Y. Mitin et al, Izv. Akad. Nauk SSSR, Ser. Khim. 11, 2666 (1968) (C.A. 70: 68721m) discloses N,N-dibenzoylglycine as a chemical intermediate without disclosing any biological activity.

A. J. Bates et al, Helv. Chim. Acta, 58 (3) 688 (1975) discloses N,N[1]-bis(benzyloxycarbonyl)-glycylglycine as a chemical intermediate without disclosing any biological activity.

SUMMARY OF THE INVENTION

The N-acyl-N-naphthoylglycines of this invention are represented by formula (I)

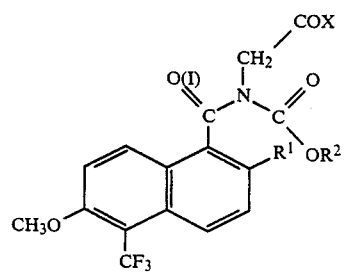

wherein $R^1$ is halogen or lower perfluoroalkoxy containing 1 to 3 carbon atoms; $R^2$ is lower alkyl preferably containing 1 to 3 carbon atoms; X is —OH or —NH$_2$, and the pharmaceutically acceptable salts thereof wherein X is —OH.

Preferred compounds of the present invention are represented by formula (I) wherein $R^1$ is fluorine, chlorine or bromine; $R^2$ is methyl or ethyl; X is —OH or —NH$_2$, and the pharmaceutically acceptable salts thereof wherein X is —OH.

The most preferred compounds of the present invention are designated:

N-[[2-fluoro-6-methoxy-5-(trifluoromethyl)-1-naphthalenyl]carbonyl]-N-(methoxycarbonyl)glycine;

[[[2-fluoro-6-methoxy-5-(trifluoromethyl)-1-naphthalenyl]carbonyl](methoxycarbonyl)amino]acetamide;

N-(ethoxycarbonyl)-N-[[2-fluoro-6-methoxy-5-(trifluoromethyl)-1-naphthalenyl]carbonyl]glycine;

N-[[2-chloro-6-methoxy-5-(trifluoromethyl)-1-naphthalenyl]carbonyl]-N-(methoxycarbonyl)glycine;

N-[[2-bromo-6-methoxy-5-(trifluoromethyl)-1-naphthalenyl]carbonyl]-N-(methoxycarbonyl)glycine;

and the pharmaceutically acceptable salts thereof.

Also included in the present invention are the chemical intermediate compounds of formula (II)

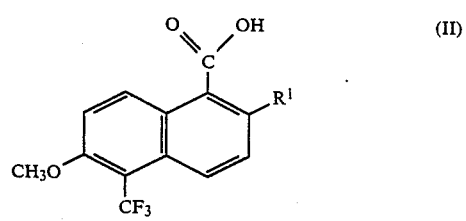

wherein $R^1$ is as defined above; and chemical intermediate compounds of formula (VI)

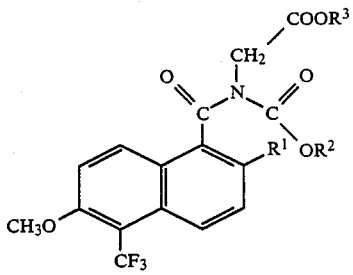

(VI)

wherein $R^1$ and $R^2$ are as defined above, and $R^3$ is t-butyl or benzyl.

The N-acyl-N-naphthoylglycines of the present invention can be prepared by the processes described hereinafter.

A method is provided for preventing or relieving diabetes mellitus associated complications in a diabetic mammal by administering to said mammal a prophylactic or alleviating amount of a compound of formula (I). Such complications include neuropathy, nephropathy, retinopathy and cataracts.

The compounds of formula (I), when admixed with a pharmaceutically acceptable carrier, form a pharmaceutical composition which can be used according to the preceding method.

DETAILED DESCRIPTION OF THE INVENTION

The compounds of this invention, represented by formula (I), can exist in rotameric forms. More explicitly, mesomerism imparts a partial double bond character to the carbonyl-nitrogen bonds. This partial double bond character leads to restricted rotation about the carbonyl-nitrogen bonds giving rise to cis and trans rotamers, the restricted rotation being augmented by the bulkiness of neighboring groups. The rotameric forms represented by structural formulas ($I^1$), ($I^2$), ($I^3$), and ($I^4$) are included within the scope of this invention:

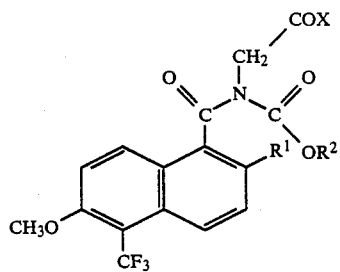

($I^1$)

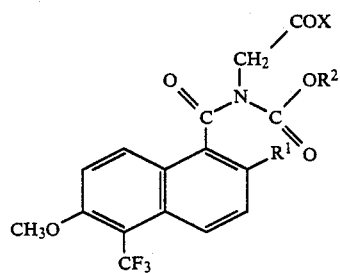

($I^2$)

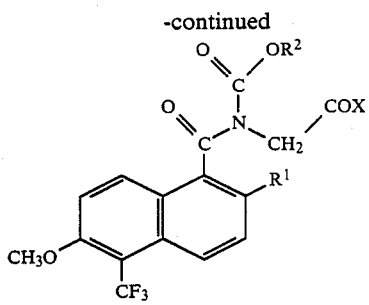

($I^3$)

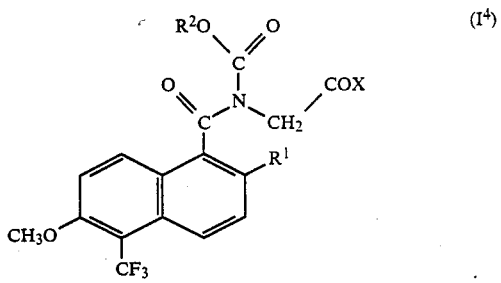

($I^4$)

wherein $R^1$, $R^2$, and X are as defined above.

For brevity, the compounds of this invention, including their rotameric forms, are referred to herein as compounds of formula (I).

The compounds of formula (I) wherein X is —OH form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltriethanol and trimethyl-monoethanol) and cyclic ammonium salts, for example the N-methylpyridinium, N-methyl-N-(2-hydroxyethyl)-morpholinium, N,N-dimethyl-morpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula (I) is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

The N-acyl-N-naphthoylglycines of this invention may be administered to mammals, for example, man, monkeys or dogs, either alone or in dosage forms, i.e., capsules or tablets, combined with pharmacologically acceptable excipients.

Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the N-acyl-N-naphthoylglycines will vary with the form of administration. Furthermore, it will vary with the particular host under treatment. Generally, treatment is initiated with small dosages substantially less than the optimal dose of the compound. In general, the compounds of this invention are most desirably administered at a concentration level that will generally afford effective results without causing any harmful or deleterious side effects. For topical administration, a 0.05–1.8% solution may be administered dropwise in the eye. The frequency of instillation varies with the subject under treatment from a drop every two or three days to once daily. For oral or parenteral administration a preferred level of dosage ranges from about 0.5 mg to about 1000 mg per kilo of body weight per day, although aforementioned variations will occur. However, a dosage level that is in the range of from about 5.0 mg to about 60 mg per kilo of body weight per day is most satisfactory.

Unit dosage forms such as capsules, tablets, pills and the like may contain from about 25 mg to about 1250 mg of the active ingredients of this invention with a pharmaceutical carrier. Thus, for oral administration, capsules can contain from between about 25 mg to about 1250 mg of the active ingredients of this invention with or without a pharmaceutical diluent. Tablets, either effervescent or noneffervescent, can contain between about 25 to 1250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents for example, magnesium stearate.

The N-acyl-N-naphthoylglycines can also be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds hereof can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 36 ed., Medical Economics Co., Oradell, N.J. U.S.A., 1982. When used in combination, the N-acyl-N-naphthoylglycines are administered as described previously. The N-acyl-N-naphthoylglycines can be administered with the oral hypoglycemic agent in the form of a pharmaceutical composition comprising effective amounts of each agent.

The aldose reductase inhibiting effects of the compounds of formula (I) were tested by employing an in vitro testing procedure similar to that described by S. Hayman and J. H. Kinoshita, J. Biol. Chem., 240,877 (1965). In the present case the procedure of Hayman and Kinoshita was modified in that the final chromatography step was omitted in the preparation of the enzyme from bovine lens. The results are tabulated in Table I under the heading In Vitro.

The aldose reductase inhibiting property of the compounds of this invention and the utilization of the compounds in preventing, diminishing and alleviating diabetic complications by lowering polyol accumulation were also demonstrable in experiments using galactosemic rats, see Dvornik et al, Science, 182, 1146 (1973). Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (rodent Laboratory Chow, Purina) and glucose at 20% (w/w %) concentration. The untreated galactosemic group and the drug-treated groups were fed a similar diet in which galactose is substituted for glucose. The test compound was either admixed to the diet or administered by gavage. In experiments involving compound administration in the diet, the average dose administered was calculated from the actual food intake of the animals in each group. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues when frozen can be kept up to two weeks before being analyzed for galactitol.

(c) The polyol determination was performed by a modification of the procedure of M. Kraml and L. Cosyns, Clin. Biochem., 2,373 (1969). Only two minor reagent changes were made: (a) the rinsing mixture was an aqueous 5% (w/v) trichloroacetic acid solution and (b) the stock solution was prepared by dissolving 25 mg of dulcitol in 100 mL of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.]

A second in vivo model examined the effect of the compounds of the present invention on sorbitol accumulation in the tissues of 14-day streptozocin (STZ) (Upjohn) diabetic rats.

In each of the studies male Sprague-Dawley rats from Charles River Labs, Kingston, NY, weighing 200 to 250 g, were used. The animals were weighed and observed for 5 days prior to the start of the study.

In each study the rats were randomly assigned by weight into groups of 15 animals except for group I which contained 8 animals. The groups were treated as follows:

Group I: Control
Group II: STZ, 110 mg/kg i.p.
Group III: STZ, 110 mg/kg i.p. followed by the reference compound tolrestat 6 mg/day given daily by gavage for 14 days, beginning on the day of induction of diabetes.
Group IV: STZ, 110 mg/kg i.p. followed by various doses of a compound of the present invention given by gavage for 14 days, beginning on the day of induction of diabetes.

Following an overnight fast (water ad lib) the animals in groups II-IV were given by i.p. injection 110 mg STZ per kg body weight. The STZ was dissolved in cold citric acid, 0.03M, pH 4.5 and injected within 5 minutes of being dissolved. Control rats (group I) were injected with buffer only. One hour following the injection, standard laboratory chow (Rodent lab chow 5001, Purina) was placed in the cages.

Two days after STZ injection plasma glucose levels (from the tail vein) were determined following a 4 hour fast. Excluded from the study were animals whose plasma glucose was below 300 mg/dl. Control animals with plasma glucose levels greater than 200 mg/dl were also excluded.

On the morning of the 14th day following STZ injection the animals were fasted 4 hours prior to sacrificing by decapitation. The blood was collected into heparin containing tubes and placed on ice. Both lenses and sciatic nerves were removed immediately, weighed, frozen, and stored at $-20°$ C. until analyzed for sorbitol. The RBCs were collected by centrifugation, the plasma was removed and the cells were washed once with 10 volumes of cold saline. The washed packed RBCs were divided into 1 mL aliquots, extracted with cold perchloric acid and the acid extracts were stored at $-20°$ C. until analyzed for sorbitol.

The tabulated results in Table I show that the N-acyl-N-naphthoylglycines of this invention show the property that they diminish the accumulation of galactitol in the lenses and sciatic nerves of rats fed galactose. The figures under L, N, and D represent the percentage decrease of galactitol accumulation in the tissues of the lens, sciatic nerve, and diaphragm, respectively, for treated rats as compared to untreated rats.

Examination of the results tabulated in Table I below shows that the N-acyl-N-naphthoylglycines of this invention are well suited as aldose reductase inhibitors and they lower polyol accumulation in tissues of diabetic or galactosemic rats. For example, N-[[2-fluoro-6-methoxy-5-(trifluoromethyl)-1-naphthal-enyl]carbony]-N-(methoxycarbonyl)glycine at a dose of 10 mg/kg/day gives comparable results to N-[[6-methoxy-5-(trifluoromethyl)-1-naphthalenyl]thioxo-methyl]-N-methylglycine at 9 mg/kg/day in the sciatic nerve. The latter compound is also known as tolrestat.

TABLE I

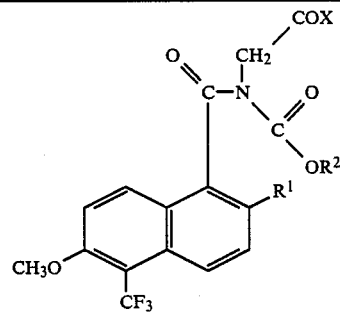

(I)

| Ex. | $R^1$ | $R^2$ | X | % Inhibition IN VITRO | | | | % Lowering dulcitol accumulation IN VIVO | | | | m.p. °C. |
|---|---|---|---|---|---|---|---|---|---|---|---|---|
| | | | | $10^{-5}$ M | $10^{-6}$ M | $10^{-7}$ M | $4 \times 10^{-8}$ M | mg/kg | (%) L | (%) N | (%) D | |
| 1 | —F | —CH$_3$ | —OH | 99 | 95 | 86 | 59 | 5 | N.S. | 50 | 52 | 160-162 |
| | | | | | | | | 10 | N.S. | 61 | 62 | |
| | | | | | | | | 14 | N.S. | 72 | 74 | |
| | | | | | | | | 15 | N.S. | 81 | 80 | |

TABLE I-continued

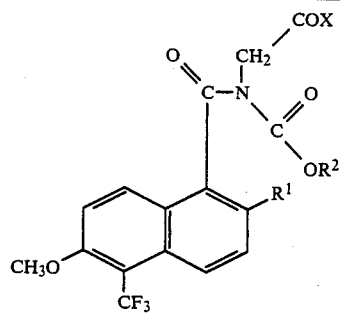

(I)

| Ex. | R¹ | R² | X | % Inhibition IN VITRO | | | | % Lowering dulcitol accumulation IN VIVO | | | | m.p. °C. |
|---|---|---|---|---|---|---|---|---|---|---|---|---|
| | | | | $10^{-5}$ M | $10^{-6}$ M | $10^{-7}$ M | $4 \times 10^{-8}$ M | mg/kg | (%) L | (%) N | (%) D | |
| 2 | —F | —CH₃ | —NH₂ | 2 | 0 | N.D. | N.D. | 5.2 | N.S. | N.S. | N.S. | 199–202 |
| 3 | —F | —C₂H₅ | —OH | 99 | 95 | 87 | 67 | 10.4 | N.S. | 43 | 23 | 135.5–138 |
| | | | | | | | | 25 | N.S | 70 | 65 | |
| 4 | —Cl | —CH₃ | —OH | 98 | 95 | 85 | 57 | 15 | N.S. | 50 | 59 | |
| | | | | | | | | 26 | N.S. | 53 | 68 | 162–165 |
| 5 | —Br | —CH₃ | —OH | 97 | 92 | 77 | 54 | 51 | N.S. | 69 | 62 | 164–167 |
| 6 | —OCH₂CF₃ | —CH₃ | —OH | 100 | 94 | 83 | 56 | 27 | N.S. | N.S. | 49 | 186–187 |
| 7 | —OCH₂CF₃ | —CH₂CH₃ | OH | 98 | 90 | 78 | 47 | 27 | N.S. | N.S. | 39 | 165.5–167 |
| 8 | —Cl | —CH₂CH₃ | —OH | 97 | 94 | 79 | 47 | 50 | N.S. | N.S | 47 | 144–146 |
| 9 | —Br | —CH₂CH₃ | —OH | 98 | 93 | 76 | 52 | 43 | N.S. | N.S. | 27 | 167–168.5 |
| (tolresat) | | | | 98 | 94 | 65 | N.D. | 9 | N.S. | 58 | 87 | 164–165 |

N.S. = not significant
N.D. = not determined
L = lens
N = nerve
D = diaphragm

| | | | | Two-Week Streptozocin-Diabetic Rat Model | | |
|---|---|---|---|---|---|---|
| | | | | | % Lowering of Sciatic Nerve Polyol Accumulation | |
| Ex. | R¹ | R² | X | Treatment (mg/kg) | Sorbitol (%) | Fructose (%) |
| 1 | —F | —CH₃ | —OH | 2 | 38 | 22 |
| | | | | 5 | 39 | 36 |
| | | | | 10 | 85 | 72 |
| | | | | 15 | 85 | 86 |
| Tolrestat | | | | 6 | 80 | 63 |

THE PROCESS

The N-acyl-N-naphthoylglycines can be prepared by the following reaction schemes:

Scheme I

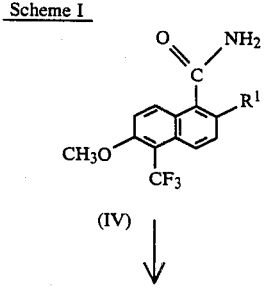

(IV)

-continued
Scheme I

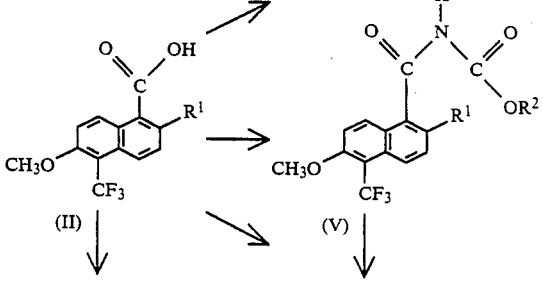

(II) (V)

Scheme I -continued

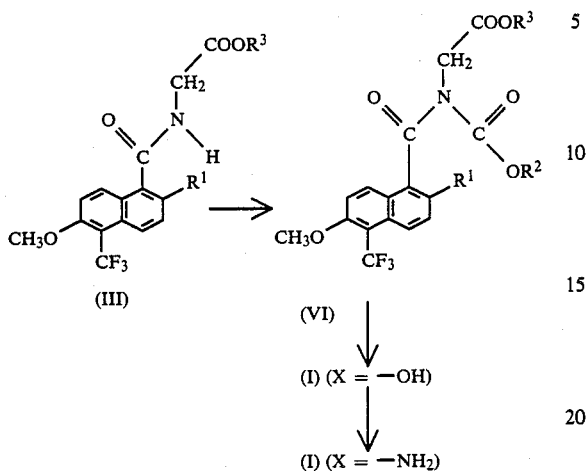

wherein $R^1$ and $R^2$ are as defined above, and $R^3$ is t-butyl or benzyl.

Scheme II

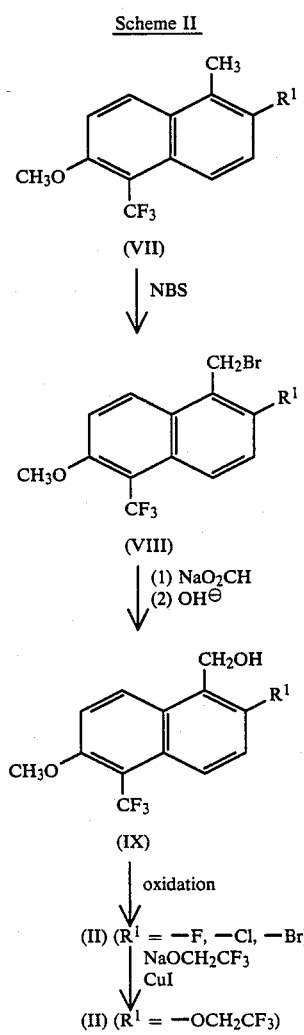

Scheme III

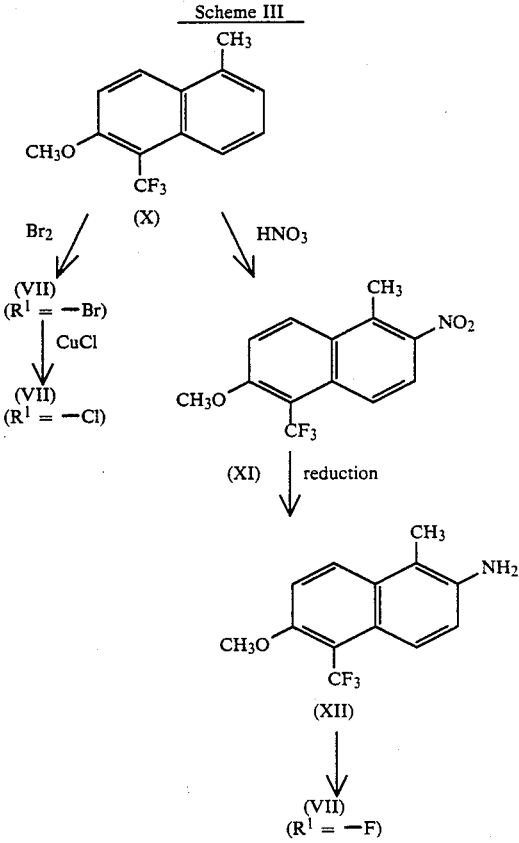

Referring to Scheme I, the carboxylic acid (II), is converted to the corresponding carboxylic acid chloride by reaction with thionyl chloride (1 to 5 eq) in a solvent such as dichloromethane, acetonitrile, chloroform, benzene, or toluene, or thionyl chloride can be used as solvent. A catalytic amount of dimethylformamide is used (0.01 to 0.03 eq). A reaction temperature ranging from 20° C. to 110° C. is used for reaction times ranging from 10 minutes to 3 hours. Other reagents that can be used under similar conditions are phosphorus trichloride and oxalyl chloride.

The carboxylic acid chloride is converted to the corresponding carboxylic acid amide (IV) by reaction of a solution of the acid chloride in an inert organic solvent such as THF, dichloromethane, benzene, or toluene with concentrated aqueous ammonium hydroxide at temperatures ranging from 0° C. to 25° C. for reaction times ranging from 5 minutes to 1 hour.

The corresponding carboxylic acid amide (IV) can alternatively be formed by reacting the acid chloride with a saturated solution of ammonia gas in an inert solvent (such as THF) at temperatures ranging from 0° C. to 25° C. for reaction times ranging from 5 minutes to 1 hour.

Reaction of (IV) with a base (sodium hydride, potassium hydride, lithium diisopropylamide, 1.0 to 1.5 eq) in anhydrous THF at temperatures ranging from 0° C. to 30° C. for 20 minutes to 1 hour, and then reaction with an alkyl chloroformate (1.0 to 1.2 eq) at temperatures ranging from 20° C. to 65° C. for 1 to 4 hours produces compound (V) wherein $R^2$ is Me or Et. When the acid (II) was reacted with ethoxycarbonyl-t-butylcarbodiimide (1.0–1.5 eq) according to the procedure of O.

Mitsunobu et al, Bull. Chem. Soc. Japan, 45, 3607 (1972), the product was (V) wherein $R^2$ is Et. The reaction was done in an inert solvent such as THF at temperatures ranging from 40° C. to 80° C. for 1 to 10 hours.

Alternatively (V) is the product when the acid chloride of (II) (prepared as previously stated) is reacted with silver cyanate (1 to 2 eq) according to the procedure of C. L. Arus et al, J. Chem. Soc., 4018 (1954), and 1091 (1957). The reaction can be conveniently performed in an inert organic solvent such as carbon tetrachloride, chloroform, dichloromethane, or benzene at temperatures ranging from 60° C. to 100° C. for reaction times from 1 hour to 24 hours. The intermediate, non-isolated isocyanate of structure

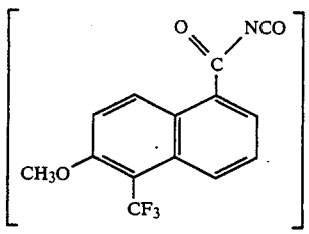

is produced. This isocyanate is reacted with the appropriate alcohol (1 to 5 eq) at temperatures ranging from 40° C. to 90° C. for times ranging from 1 to 3 hours to produce the compounds (V) wherein $R^2$ is lower alkyl.

Reaction of (V) in THF or DMF with 1.0 to 1.3 eq of a base such as sodium hydride, potassium hydride, lithium diisopropylamide (in THF) at temperatures between 0° C. and 60° C. from 10 minutes to 4 hours and then reaction with tert-butyl bromoacetate or tert-butyl chloroacetate (1.0 to 2.0 eq) at temperatures from 0° C. to 65° C. for a period of 30 minutes to 3 days produces the compounds (VI).

The carboxylic acid (II) is converted to a carboxyl activated form such as the acid chloride (mentioned previously) or the 1-benzotriazolyl ester. Description of carboxyl activating groups are found in general textbooks of peptide chemistry; for example, K. D. Kopple, "Peptides and Amino Acids," W. A. Benjamin, Inc., New York, 1966, pp 45-51, and E. Schroder and K. Luoke, "The peptides," Vol. 1, Academic Press, New York, 1965, pp 77-128. Examples of the activated form of the terminal carboxyl are the acid chloride, acid bromide, anhydride, azide, activated ester, or O-acyl urea obtained from a dialkylcarbodiimide. Preferred activated forms of the carboxyl are the acid chloride or the 1-benzotriazolyl, 2,4,5-trichlorophenyl, or succinimido activated esters.

The carboxyl activated form of formula (II) is then reacted with one to three molar equivalents of the glycine ester hydrochloride and with one to five equivalents of triethylamine to give the product of formula (III). The reaction is conveniently performed in an anhydrous solvent such as tetrahydrofuran or dimethylformamide at temperatures ranging from 15° C. to 40° C. and at times ranging from 2 to 24 hours.

Reaction of (III) in THF with 1 to 3 eq of a base such as sodium hydride, potassium hydride or lithium diisopropylamide at temperatures between 0° C. and 60° C. for 10 minutes to 4 hours and then reaction with an alkyl chloroformate such as methyl or ethyl chloroformate (1 to 2 eq) at 0° C. to 45° C. for a period of 10 minutes to 24 hours produced compounds (VI).

Alternatively a base, such as solid sodium hydroxide or solid potassium hydroxide (1.0 to 2.0 eq), is added to an acetone solution of (III) at −40° C. and stirred for 30 minutes to 1 hour. To this is added an alkyl chloroformate such as methyl chloroformate or ethyl chloroformate (1.0 to 2.0 eq) and the reaction temperature maintained at 20° C. to 30° C. for 1 hour to 4 hours to produce the compounds (VI).

An alkoxycarbonylglycine ester such as methoxycarbonylglycine, t-butyl ester can be reacted with a base such as sodium or potassium hydride (1 to 1.5 eq) in an inert solvent such as THF to produce the corresponding anion of formula (XIII).

$$[R^2OCO\ominus NCH_2CO_2R^3] \qquad (XIII)$$

wherein $R^2$ and $R^3$ are as defined above.

The anion (XIII) (1 to 2 eq) can then be reacted with the acid chloride of acid (II) in an inert solvent such as THF at temperatures ranging from 0° C. to 40° C. and at times ranging from 5 minutes to 5 hours.

For the conversion of compounds of formula (VI) wherein $R^3$ is t-butyl to compounds of formula (I) wherein X is —OH, (VI) is reacted with an organic protic acid such as trifluoroacetic acid (1 eq up to use as solvent) or formic acid (5 eq up to use as solvent) or the reaction is carried out in a halocarbon solvent, such as dichloromethane, chloroform, or carbon tetrachloride at temperatures from 20° C. to 40° C. for periods of 1 hour to 3 hours to produce the compounds (I) wherein X is —OH.

Trimethylsilyliodide (1 to 10 eq) in a halocarbon solvent at temperatures from 20° C. to 40° C. for periods of 1 to 3 hours was also used to remove the protective group and produce the compounds (I) wherein X is —OH.

If $R^3$ of compound (VI) is $CH_2Ph$ then (VI) is catalytically hydrogenated at 14 to 60 psi $H_2$ pressure, ambient temperatures for 10 minutes to 4 hours using 10% palladium on carbon as catalyst (5 to 20% by weight).

For the conversion of compounds of formula (I) wherein X is —OH to compounds of formula (I) wherein X is —$NH_2$, the compound of formula (I) wherein X is —OH is converted to the acid chloride using methods discussed for generation of the acid chloride of (II). The acid chloride of (I) is then reacted with ammonia gas dissolved in an inert solvent such as THF or ether at temperatures ranging from 0° C. to 30° C. for 1 to 30 minutes to produce the compound (I) wherein X is —$NH_2$.

Referring to Scheme (II), the compound of formula (VII) is converted to the compound of formula (VIII) by reaction with N-bromosuccinimide (1 to 3 eq) with catalytic benzoyl peroxide (0.001 to 0.1 eq) in an inert solvent such as carbontetrachloride at temperatures ranging from 60° C. to 100° C. at times ranging from 30 minutes to 40 hours.

The conversion of compound (VIII) to compound (IX) is carried out by reaction of (VIII) with sodium formate (1 to 10 eq) in an aqueous alcoholic solvent at 50° C. to 100° C. for 30 minutes to 4 hours followed by an aqeuous base work up (i.e. sodium or potassium hydroxide).

Other hydrolyzing conditions can be used such as sodium carbonate in aqueous alcohol.

For the conversion of (IX) to (II) wherein $R^1=$—F, —Cl, —Br, excess chromium trioxide in sulfuric acid-water (a mixture known as Jones reagent) was used in acetone at temperature from 0° C. to 30° C. at times ranging from 30 minutes to 4 hours.

Alternatively excess potassium permanganate could be used as the oxidant in aqueous t-butyl alcohol at 70° C. to 100° C. for 30 minutes to 2 hours or in a biphasic mixture of toluene and water with catalytic tetra-N-butyl ammonium halide or 18-Crown-6 polyether at temperatures ranging from 20° C. to 100° C. and for times ranging from 1 hour to 4 days.

For the conversion of compound (II) wherein $R^1=$—Br to compound (II) wherein $R^1=$—OCH$_2$CF$_3$, the compound (II) wherein $R^1=$—Br was treated with sodium trifluoroethoxide which was generated by reacting trifluoroethanol with an equivalent amount of sodium hydride. Alternatively, sodium metal, potassium hydride, or potassium t-butoxide could be used to generate the metal trifluoroethoxide.

This metal trifluoroethoxide (1 to 15 eq) was reacted with the bromo acid compound (II), wherein R=—Br in the presence of copper (I), such as copper (I) iodide (1 to 15 eq). The reaction was done conveniently in THF solvent or in a polar aprotic solvent such as HMPA or DMF at temperatures ranging from 40° C. to 120° C. for 30 minutes to 6 hours.

Referring to Scheme (III), the compound (X) is converted to the compound (VII) wherein R=—Br by reaction with bromine (1 to 2 eq) in a solvent such as acetic acid or carbontetrachloride at 0° C. to 40° C. for times ranging from 1 hour to 30 hours.

The conversion of compounds of formula (VII) wherein R=—Br to compounds of formula (VII) wherein R=—Cl is carried out by reacting compound (VII) wherein R=—Br with copper (I) chloride (1 to 10 eq) in an inert polar aprotic solvent such as DMSO, DMF or HMPA at temperatures ranging from 150° C. to 250° C.

The compound (X) was converted to the compound (XI) by reacting the compound (X) with fuming nitric acid (90% S.G.=1.5, 1 to 10 equivalents) in acetic anhydride at temperatures ranging from −20° C. to 25° C. and times ranging from 1 to 3 hours.

Other reagents that can be used are concentrated nitric acid (70%) at temperatures ranging from 0° C. to 30° C., and times ranging from 30 minutes to 1.5 hours, nitric acid in acetic acid at 25° C., sodium nitrate in trifluoroacetic acid at 0° C. and ammonium nitrate in trifluoroacetic anhydride at 25° C.

Reduction of compound (XI) to (XII) is carried out by catalytic amounts of 10% palladium on carbon (5 to 20% by weight) in an alcoholic solvent or ethyl acetate at room temperature at 20 to 60 psi H$_2$ pressure. Alternatively, zinc in acid, iron powder or tin (II) chloride in acid can be used.

Conversion of compound (XII) to compound (VII) wherein $R^1=$—F is carried out with sodium nitrite (1 to 3 eq) in hydrogen fluoride-pyridine at temperatures ranging from −78° C. to 65° C. and times ranging from 30 minutes to 4 hours.

Alternatively, reaction of the amine (XII) with sodium nitrite (1 to 3 eq) in aqueous tetrafluoroboric acid at 0° C. to 30° C. for 20 minutes to 1 hour to provide the corresponding diazonium tetrafluoroborate ((VII) wherein $R^1=N_2^{\ominus}BF_4^{\oplus}$, which is then pyrollyzed neat or in an inert solvent such as xylenes or chlorobenzene at temperatures ranging from 100° C. to 200° C. and times ranging from 10 minutes to 1 hour.

The following Examples further illustrate this invention.

EXAMPLE 1

N-[[2-Fluoro-6-methoxy-5-(trifluoromethyl)-1-naphthalenyl]carbonyl]-N-(methyoxycarbonyl)glycine (I): $R^1=$—F; $R^2=$—CH$_3$; X=—OH Step (1) Preparation of N-[[2-Fluoro-6-methoxy-5-(trifluoromethyl)-1-naphthalenyl]carbonyl]glycine, 1,1-Dimethylethyl Ester A solution of 2-fluoro-6-methoxy-5-(trifluoromethyl)-1-naphthoic acid (17.0 g, 59.0 mmol, prepared by the process of Example 10), 1-hydroxybenzotriazole (11.96 g, 1.5 eq) and 1-(3-dimethylaminopropyl)-3-ethylcarbodiimide hydrochloride (13.57 g, 1.2 eq) in dry DMF (375 mL) was stirred at room temperature under a dry N$_2$ atmosphere for 1.25 hours. Glycine, t-butylester hydrochloride (19.78 g, 2.0 eq) and triethylamine (27.1 mL, 3.3 eq) were added and the resulting suspension was stirred for 30 minutes. The reaction mixture was poured into water (3 L) and extracted with ether (3×300 mL). The combined ether extracts were concentrated and the solid product was washed well with water and dried in vacuo to provide the title compound as a white solid (21.98 g, 93%). A small amount was flash chromatographed (99:1 CHCl$_3$:CH$_3$CN) for analysis, m.p. 144°–146° C.

NMR (CDCl$_3$, 400 MHz): δ 1.50 (s, 9H, OC(CH$_3$)$_3$), 3.98 (s, 3H, OCH$_3$), 4.22 (d, 2H, J=5.5 Hz, NHCH$_2$), 6.50 (m, 1H, NHCH$_2$), 7.35 (m, 2H, ArH), 8.25 (m, 1H, ArH), 8.35 (d, 1H, ArH);

IR (CHCl$_3$, cm$^{-1}$): 3450, 3430 (NH), 1735 (CO$_2$tBu), 1665 (CON);

Anal. Calcd.: C, 56.86; H, 4.77; N, 3.49%. Found: C, 56.96; H, 4.66; N, 3.62%.

Step (2) Preparation of N-[[2-Fluoro-6-methoxy-5-(trifluoromethyl)-1-naphthalenyl]carbonyl]-N-(methoxycarbonyl)glycine, 1,1-Dimethylethyl Ester Sodium hydride (80% dispersion in mineral oil, 1.81 g, 1.1 eq) was added to a stirred, room temperature solution of N-[[2-fluoro-6-methoxy-5-(trifluoromethyl)-1-naphthalenyl]carbonyl]glycine, 1,1-dimethylethyl ester (21.98 g, 54.76 mmol) in dry THF (450 mL) under a dry N$_2$ atmosphere. The suspension was heated in a 50° C. oil bath until hydrogen evolution ceased (approximately 2 hours). The reaction mixture was cooled to 0°–5° C. and a solution of methyl chloroformate (5.76 mL, 1.36 eq) in dry THF (150 mL) was added dropwise over a 20 minute period. The reaction mixture was then warmed to room temperature and stirred for 30 minutes. The reaction mixture was quenched with saturated aqueous NH$_4$Cl and diluted with ether (500 mL). Silica gel (100 mL) was added and the solvents were removed in vacuo. The silica absorbate was flash chromatographed (gradient elution 4:1 to 7:3 petroleum ether:ethyl acetate, silica) to provide the title compound as a white solid (18.79 g, 75%) and starting material (3.07 g, 14%). A small portion was recrystallized from petroleum ether:ether for analysis; m.p. 111°–114° C.

NMR (CDCl$_3$, 200 MHz): δ 1.54 (s, 9H, OC(CH$_3$)$_3$), 3.57 (s, 3H, CO$_2$CH$_3$), 3.99 (s, 3H, OCH$_3$), 4.65 (m, 2H, NCH$_2$), 7.35 (m, 2H, ArH), 8.12 (d, 1H, ArH), 8.28 (m, 1H, ArH);

IR (neat, cm$^{-1}$): 1755, 1740, 1690 (C=O);

Anal. Calcd.: C, 54.90; H, 4.61; N, 3.05%. Found: C, 55.09; H, 4.45; N, 3.12%.

Step (3) Preparation of N-[[2-Fluoro-6-methoxy-5-trifluoromethyl)-1-naphthalenyl]carbonyl]-N-(methoxycarbonyl)glycine N-[[2-Fluoro-6-methoxy-5-trifluoromethyl)-1-naphthalenyl]carbonyl]-N-(methoxycarbonyl)glycine, 1,1-dimethylethyl ester (18.79 g, 40.90 mmol) was suspended in dry formic acid (575 mL) and stirred at room temperature. Dissolution occurred within 15 minutes. After 1 hour the reaction was complete. The reaction mixture was concentrated in vacuo and added to water (4 L). This aqueous suspension was stirred with heating (~40°-50° C.) for 30 minutes to insure proper solidification. The resulting solid was collected and washed with water (2×150 mL) and dried in vacuo at 100° C. to provide the title compound as a white solid in 94% yield, m.p. 160°-162° C.

NMR (d$^6$DMSO, 400 MHz): δ 3.53 (s, 3H, CO$_2$CH$_3$), 4.01 (s, 3H, OCH$_3$), 4.62 (m, 1H, NCH$^1$H$^2$), 4.71 (m, 1H, NCH$^1$H$^2$), 7.63 (t, 1H, ArH), 7.72 (d, 1H, ArH), 8.15 (m, 2H, ArH);

IR (KBr, cm$^{-1}$): 3600-2450 (CO$_2$H), 1765, 1695 (C=O);

MS (z/e): 403 (48%), 271 (100%);

Anal. Calcd.: C, 50.63; H, 3.25; N, 3.47%. Found: C, 50.81; H, 3.44; N, 3.62%.

EXAMPLE 2

[[[2-Fluoro-6-methoxy-5-(trifluoromethyl)-1-naphthalenyl]carbonyl](methoxycarbonyl)amino]acetamide (I): R$^1$=—F; R$^2$=—CH$_3$; X=—NH$_2$ Dimethyl formamide (6 μL, 0.067 eq) and oxalyl chloride (130 μL, 1.2 eq) were added to a stirred solution of N-[[2-fluoro-6-methoxy-5-(trifluoromethyl)-1-naphthalenyl]carbonyl]-N-(methoxycarbonyl)glycine in anhydrous methylene chloride (2.5 mL) at 0° C. under a dry nitrogen atmosphere. After 5 minutes, the reaction was warmed to room temperature. After 1¾ hours, the organics were removed. The residue was dissolved in anhydrous ether (30 mL) at 0° C. and ammonia gas was bubbled in for 1 minute. The reaction was immediately quenched with hexane (30 mL). The solid was collected by suction filtration and suspended in ethyl acetate (75 mL). The ethyl acetate phase was washed with water (2×25 mL), dried with magnesium sulfate, and the ethyl acetate was removed. The solid was combined with that from another run and recrystallized in chloroform:petroleum ether to provide the title compound as a white solid (325 mg, 54% combined yield), m.p. 199°-202° C.

NMR (DMSO-d$^6$, 400 MHz): δ 3.49 (s, 3H, CO$_2$CH$_3$), 4.00 (s, 3H, ArOCH$_3$), 4.42 (d, 1H, J=16.4 Hz, NCH$^1$H$^2$CONH$_2$), 4.66 (d, 1H, J=16.4 Hz, NCH$^1$H$^2$CONH$_2$), 7.27 (s, 1H, CONH$^1$H$^2$), 7.62 (t, 1H, J=9.4 Hz, ArH), 7.71 (d, 2H, J=9.8 Hz, ArH and CONH$^1$H$^2$), 8.11 (m, 1H, ArH), 8.35 (d, 1H, J=9.4 Hz, ArH);

IR (KBr, cm$^{-1}$): 3420 and 3330 (NH$_2$), 1742 (C=O), 1678 (2C=O), 1615 and 1588 (C=C);

MS (z/e): 402 (M+, 21%), 271 (100%);

Anal. Calcd.: C, 50.75; H, 3.51; N, 6.96%. Found: C, 50.94; H, 3.78; N, 6.86%.

EXAMPLE 3

N-(Ethoxycarbonyl)-N-[[2-fluoro-6-methoxy-5-(trifluoromethyl)-1-naphthalenyl]carbonyl]glycine (I): R$^1$=—F; R$^2$=—C$_2$H$_5$; X=—OH Step (1) Preparation of N-[[2-Fluoro-6-methoxy-5-(trifluoromethyl)-1-naphthalenyl]carbonyl]carbamic Acid, Ethyl Ester According to the procedure of O. Mitsunobu et al, Bull. Chem. Soc. Japan, 45, 3607 (1972), a solution of 2-fluoro-6-methoxy-5-(trifluoromethyl)-1-naphthoic acid (2.30 g, 8.00 mmol, prepared by the process of Example 10), and ethoxycarbonyl-t-butylcarbodiimide (1.50 g, 1.1 eq) in anhydrous THF (40 mL) was heated to reflux for 2½ hours under a dry nitrogen atmosphere. The reaction was cooled to room temperature and the THF was removed. The crude product was triturated with ether to provide the title compound as an off white solid (2.37 g, 82%). A small sample was recrystallized from CHCl$_3$:petroleum ether for analysis, m.p. 172°-174° C.

NMR (CDCl$_3$, 200 MHz): δ 1.24 (t, 3H, J=6.9 Hz, CO$_2$CH$_2$CH$_3$), 3.98 (s, 3H, ArOCH$_3$), 4.18 (q, 2H, J=6.8 Hz, CO$_2$CH$_2$CH$_3$), 7.34 (m, 2H, 2ArH), 7.94 (s, 1H, NH), 8.14 (d, 1H, J=9.5 Hz, ArH), 8.33 (m, 1H, ArH);

IR (CHCl$_3$, cm$^{-1}$): 3400 (NH), 1781 (C=O), 1692 (C=O), 1611 and 1583 (C=C);

Exact Mass: Calcd.=359.0785; Found=359.0780

Step (2) Preparation of N-[[2-Fluoro-6-methoxy-5-(trifluoromethyl)-1-naphthalenyl]carbonyl]-N-(ethoxycarbonyl)glycine, 1,1-Dimethylethyl Ester Sodium hydride (80% by weight dispersion in mineral oil 0.208 g, 1.1 eq) was added to a stirred solution of N-[[2-fluoro-6-methoxy-5-(trifluoromethyl)-1-naphthalenyl]carbonyl]carbamic acid, ethyl ester (2.26 g, 6.29 mmol) in anhydrous tetrahydrofuran (75 mL) at room temperature under a dry nitrogen atmosphere. After 45 minutes, the t-butyl bromoacetate (1.52 mL, 1.5 eq) was added and the reaction was heated to 60° C. After 1¼ hours of heating, the reaction was cooled to room temperature and the THF was removed. The residue was suspended in ether (150 mL), washed with water (2×75 mL) and saturated aqueous NaCl (1×50 mL), dried with MgSO$_4$, and the ether was removed. The crude oil was flash chromatographed (4:1 petroleum ether:ethyl acetate, silica) then triturated with petroleum ether (3×30 mL) to provide the title compound as a white powder (2.40 g, 81%), m.p. 81°-83° C.

NMR (CDCl$_3$, 200 MHz): δ 0.81 (t, 3H, J=7.4 Hz, CO$_2$CH$_2$CH$_3$), 1.53 (s, 9H, CO$_2$C(CH$_3$)$_3$), 3.98 (m, 5H, ArOCH$_3$ and CO$_2$CH$_2$CH$_3$), 4.65 (broad d, 2H, NCH$_2$CO$_2$), 7.31 (t, 1H, J=9.5 Hz, ArH), 7.40 (d, 1H, J=9.5 Hz, ArH), 8.14 (d, 1H, J=9.2 Hz, ArH), 8.23 (m, 1H, ArH);

IR (CHCl$_3$, cm$^{-1}$): 2990 (CH), 1740 (C=O), 1675 (C=O), 1610 and 1580 (C=C);

Anal. Calcd.: C, 55.81; H, 4.90, N, 2.96%. Found: C, 55.86; H, 5.10; N, 2.97%.

Step (3) N-(Ethoxycarbonyl)-N-[[2-fluoro-6-methoxy-5-(trifluoromethyl)-1-naphthalenyl]carbonyl]glycine A suspension of N-[[2-fluoro-6-methoxy-5-(trifluoromethyl)-1-naphthalenyl]carbonyl]-N-(ethoxycarbonyl)glycine, 1,1-dimethylethyl ester (2.40 g, 5.07 mmol) in formic acid (90 mL) was stirred at room temperature under a dry nitrogen atmosphere. After 10 minutes, dissolution occurred. After 1½ hours, the reaction solution was diluted with water (1 L). The resultant suspension was stirred rapidly for 45 minutes, then filtered. The solid was washed with water (3×20 mL), air dried, and recrystallized from benzene:petroleum ether to provide the title compound as white needles (1.21 g, 57%), m.p. 135.5°–138° C.

NMR (DMSO-d$^6$, 400 MHz): δ 0.71 (t, 3H, J=7.1 Hz, CO$_2$CH$_2$CH$_3$), 3.88 (q, 2H, J=6.9 Hz, CO$_2$CH$_2$CH$_3$), 4.01 (s, 3H, ArOCH$_3$), 4.64 (dd, 2H, J=16.3 and 24.4 Hz, NCH$_2$CO$_2$H), 7.64 (t, 1H, J=9.3 Hz, ArH), 7.74 (d, 1H, J=9.5 Hz, ArH), 8.16 (d, 2H, J=9.4 Hz, 2ArH); ;

IR (KBr, cm$^{-1}$): 1755 (CO$_2$H), 1702 (C=O), 1682 (C=O), 1609 and 1572 (C=C);

MS (CI): 418 (32%), 398 (33%), 323 (75%), 271 (100%);

Anal. Calcd.: C, 51.81; H, 3.62; N, 3.36%. Found: C, 51.90; H, 3.87; N, 3.32%.

EXAMPLE 4

N-[[2-Chloro-6-methoxy-5-(trifluoromethyl)-1-naphthalenyl]carbonyl]-N-(methoxycarbonyl)glycine (I): R$^1$=—Cl; R$^2$=—CH$_3$; X=—OH Step (1) Preparation of N-[[2-Chloro-6-methoxy-5-(trifluoromethyl)-1-naphthalenyl]carbonyl]glycine, 1,1-Dimethylethyl Ester 1-Hydroxybenzotriazole hydrate (2.45 g, 1.5 eq) and 1-(3-dimethylaminopropyl)-3-ethylcarbodiimide hydrochloride (2.78 g, 1.2 eq) was added to a stirred solution of 2-chloro-6-methoxy-5-(trifluoromethyl)naphthoic acid (3.69 g, 12.11 mmol, prepared by the process of Step 3, Example 12) in dry dimethylformamide (78 mL). After stirring 1½ hours at room temperature, glycine t-butyl ester hydrochloride (4.06 g, 2 eq) and triethylamine (dried over KOH, 5.8 mL, 3.3 eq) were added. After stirring 3 hours the reaction mixture was diluted with water (1 L) and extracted with ether (3×350 mL). Silica gel was added to the extracts and the solvent was removed. The absorbate was flash chromatographed (70:30 petroleum ether:ethyl acetate) to give the title compound as a white solid (3.95 g, 80%), m.p. 166°–167° C.

NMR (CDCl$_3$, 200 MHz): δ 1.50 (s, 9H, C(CH$_3$)$_3$), 3.98 (s, 3H, OCH$_3$), 4.22 (d, 2H, J=4 Hz, NCH$_2$), 6.34 (s, 1H, NH), 7.38 (d, 1H, J=10 Hz, ArH), 7.48 (d, 1H, J=10 Hz, ArH), 8.15 (d, 2H, J=9 Hz, ArH);

IR (CHCl$_3$, cm$^{-1}$): 1730 (C=O), 1660 (C=O);

Exact Mass: Calcd.=417.09557; Found=417.0984

Step (2) Preparation of N-[[2-Chloro-6-methoxy-5-(trifluoromethyl)-1-naphthalenyl]carbonyl]-N-(methoxycarbonyl)glycine, 1,1-Dimethylethyl Ester To a suspension of potassium hydride (0.9 g, 1.2 eq, 35% by weight dispersion in mineral oil) in dry tetrahydrofuran (20 mL) under argon at room temperature was added dropwise a solution of N-[[2-chloro-6-methoxy-5-(trifluoromethyl)-1-naphthalenyl]carbonyl]glycine, 1,1-dimethylethyl ester (2.73 g, 6.53 mmol) in dry THF (30 mL). After stirring 25 minutes the reaction was cooled in an ice bath and a solution of methyl chloroformate (0.7 mL, 1.4 eq) in dry THF (18 mL) was added dropwise over a period of 20 minutes. After stirring 1 hour the reaction was quenched with saturated aqueous ammonium chloride and diluted with ether (300 mL). The ether layer was separated, and dried over magnesium sulfate. Silica gel was added and the ether was removed. The silica absorbate was flash chromatographed (4:1 petroleum ether:EtOAc) to give the title compound as a white solid (2.10 g, 67%). A small sample was further purified by trituration with petroleum ether, m.p. 117°–118° C.

NMR (CDCl$_3$, 200 MHz): δ 1.54 (s, 9H, C(CH$_3$)$_3$), 3.55 (s, 3H, COOCH$_3$), 3.98 (s, 3H, ArOCH$_3$), 4.48 (d, 1H, J=17 Hz, NCH$^1$H$^2$), 4.85 (d, 1H, J=17 Hz, NCH$^1$H$^2$), 7.40 (d, 1H, J=10 Hz, ArH), 7.48 (d, 1H, J=10 Hz, ArH), 8.10 (d, 1H, J=10 Hz, ArH), 8.17 (d, 1H, J=10 Hz, ArH);

IR (CHCl$_3$, cm$^{-1}$): 1740 (C=O), 1725 (C=O), 1625 (C=O);

Anal. Calcd.: C, 53.01; H, 4.45; N, 2.94%. Found: C, 52.89; H, 4.40; N, 2.63%.

Step (3) Preparation of N-[[2-Chloro-6-methoxy-5-(trifluoromethyl)-1-naphthalenyl]carbonyl]-N-(methoxycarbonyl)glycine N-[[2-Chloro-6-methoxy-5-(trifluoromethyl)-1-naphthalenyl]carbonyl]-N-(methoxycarbonyl)glycine, 1,1-dimethylethyl ester (3.10 g, 6.51 mmol) was suspended in formic acid (122 mL) under nitrogen at room temperature and stirred for 1½ hours. The reaction mixture was diluted with water (1½ L) and extracted with ether (2×200 mL). The extracts were combined, dried over magnesium sulfate and concentrated. The residue was recrystallized from benzene to afford the title compound as a white solid (1.76 g, 64%), m.p. 162°–165° C.

NMR (d$^6$DMSO, 400 MHz): δ 3.52 (s, 3H, COOCH$_3$), 4.02 (s, 3H, ArOCH$_3$), 4.61 (d, 1H, J=7 Hz, NCH$^1$H$^2$), 4.73 (d, 1H, J=7 Hz, NCH$^1$H$^2$), 7.70 (d, 1H, J=4 Hz, ArH), 7.72 (d, 1H, J=4 Hz, ArH), 8.09 (d, 1H, J=10 Hz, ArH), 8.12 (d, 1H, J=10 Hz, ArH);

IR (KBr, cm$^{-1}$): 1761 (C=O), 1738 (C=O), 1700 (C=O), 1622 and 1595 (C=C);

MS (z/e): 419 (6%), 385 (21%), 384 (100%), 287 (42%), 132 (30%), 129 (29%);

Anal. Calcd.: C, 48.65; H, 3.12; N, 3.34%. Found: C, 48.60; H, 2.99; N, 3.34%.

EXAMPLE 5

N-[[2-Bromo-6-methoxy-5-(trifluoromethyl)-1-naphthalenyl]carbonyl]-N-(methoxycarbonyl)glycine (I): R$^1$=—Br; R$^2$=—CH$_3$; X=—OH Step (1) Preparation of 2-Bromo-6-methoxy-5-(trifluoromethyl)-1-naphthalenecarboxamide A suspension of 2-bromo-6-methoxy-5-trifluoromethyl-1-naphthoic acid (2.0 g, 5.73 mmol, prepared by the process of Example 11, Step 2), thionyl chloride (11 mL) and dimethylformamide (40 μl, 0.095 eq) was heated with stirring at 60° C. under a dry N$_2$ atmosphere for 35 minutes. The reaction mixture was cooled to room temperature and the thionyl chloride was removed. The solid residue was dissolved in THF (20 mL) and this solution was added dropwise to stirred, cold (0°–5° C.) ammonium hydroxide over a 5 minute period. After 15 minutes water (100 mL) was added and the suspension was filtered. The solid was washed with water and dried in vacuo to yield the title compound as a white solid in (1.80 g, 90%)

NMR (d$^6$DMSO, 200 MHz): δ 3.99 (s, 3H, OCH$_3$), 7.88 (m, 2H, ArH), 7.90–8.25 (m, 4H, NH$_2$, ArH)

Step (2) N-[[2-Bromo-6-methoxy-5-(trifluoromethyl)-1-naphthalenyl]carbonyl]carbamic Acid, Methyl Ester 2-Bromo-6-methoxy-5-(trifluoromethyl)-1-naphthalenecarboxamide (4.18 g, 12.01 mmol) was added to a stirred suspension of sodium hydride (50% dispersion in mineral oil, 632 mg, 1.1 eq) in anhydrous THF (110 mL) precooled in an ice bath under a dry N$_2$ atmosphere. The ice bath was removed and the suspension was stirred at ambient temperature for 30 minutes, warmed to 40° C. and stirred an additional 20 minutes. The reaction mixture was cooled to room temperature and methyl chloroformate (0.93 mL, 1.0 eq) in THF (25 mL) was added dropwise over a 10 minute period. After an additional 20 minutes, saturated aqueous NH$_4$Cl (35 mL) was added. The reaction mixture was added to water (400 mL) and extracted with ether (2×300 mL). The combined ether extracts were washed with saturated aqueous NaCl (300 mL). Silica gel (25 mL) was added to the ether solution and the solvent was removed. The silica absorbate was flash chromatographed (3:2 petroleum ether:ethyl acetate, silica) to provide the title compound as a white solid (2.71 g, 56%) m.p. 180°–182° C.

NMR (CDCl$_3$, 200 MHz): δ 3.75 (s, 3H, CO$_2$CH$_3$), 4.01 (s, 3H, OCH$_3$), 7.38 (d, 1H, ArH), 7.68 (d, 1H, ArH), 7.52 (d, 1H, ArH), 8.17 (d, 1H, ArH);

IR (CHCl$_3$, cm$^{-1}$): 3400 (NH), 1770, 1700 (CONCO);

Anal. Calcd.: C, 44.36; H, 2.73, N, 3.45%. Found: C, 44.28; H, 2.42; N, 3.30%.

Step (3) Preparation of N-[[2-Bromo-6-methoxy-5-(trifluoromethyl)-1-naphthalenyl]carbonyl]-N-(methoxycarbonyl)glycine, 1,1-Dimethylethyl Ester Sodium hydride (2.61 g, 6.43 mmol) was added to a stirred solution of N-[[2-bromo-6-methoxy-5-(trifluoromethyl)-1-naphthalenyl]carbonyl]carbamic acid, methyl ester (2.61 g, 6.43 mmol) in dry THF (95 mL) at room temperature under a dry N$_2$ atmosphere. After 1 hour, tert-butyl bromoacetate (1.56 mL, 1.5 eq) was added and the reaction mixture was heated at 60° C. for 2.5 hours. The reaction mixture was cooled to room temperature and the THF was removed. Water (100 mL) was added and the resulting solid was filtered. The resulting solid was washed with water and then petroleum ether and dried in vacuo to provide the title compound as a white solid (2.81 g, 84%). A small portion was recrystallized from petroleum ether:ether, m.p. 126°–128° C.

NMR (CDCl$_3$, 200 MHz): δ 1.54 (s, 9H, C(CH$_3$)$_3$), 3.54 (s, 3H, CO$_2$CH$_3$), 3.98 (s, 3H, OCH$_3$), 4.48 (d, 1H, J=17.2 Hz, NCH$^1$H$^2$), 4.86 (d, 1H, J=17.2 Hz, NCH$^1$H$^2$), 7.38 (d, 1H, ArH), 7.61 (d, 1H, ArH), 8.09 (m, 2H, ArH);

IR (CHCl$_3$, cm$^{-1}$): 1750, 1690 (C=O);

Anal. Calcd.: C, 48.48; H, 4.07; N, 2.69%. Found: C, 48.61; H, 4.37; N, 2.60%.

Step (4) Preparation of N-[[2-Bromo-6-methoxy-5-(trifluoromethyl)-1-naphthalenyl]carbonyl]-N-(methoxycarbonyl)glycine Formic acid (100 mL) was added to N-[[2-bromo-6-methoxy-5-(trifluoromethyl)-1-naphthalenyl]carbonyl]-N-(methoxycarbonyl)glycine, 1,1-dimethyl ester (2.67 g, 5.13 mmol), and the suspension was stirred at room temperature under a dry N$_2$ atmosphere. Dissolution occurred within 20 minutes. After 2 hours the reaction mixture was added to rapidly stirred water (1.2 L). The resulting solid was removed by filtration and washed well with water. The solid was taken up in ethyl acetate (200 mL), dried (MgSO$_4$) and the solvent was removed. The resulting oil was triturated with petroleum ether to provide the title compound as a white solid (1.84 g, 77%). This solid was further purified by recrystallization from petroleum ether:chloroform (0.87 g, 37%), m.p. 164°–166° C.

NMR (d$^6$DMSO, 400 MHz): δ 3.52 (s, 3H, CO$_2$CH$_3$), 4.02 (s, 3H, OCH$_3$), 4.60 (d, 1H, J=17.5 Hz, —NCH$^1$H$^2$), 4.74 (d, 1H, J=17.5 Hz, —NCH$^1$H$^2$), 7.70 (d, 1H, J=9.5H, ArH), 7.81 (d, 1H, J=4.5 Hz, ArH), 8.01 (dm, 1H, ArH), 8.14 (d, 1H, J=9.5 Hz, ArH);

IR (KBr, cm$^{-1}$): 3650–2500 (CO$_2$H), 1770, 1740, 1730, 1695 (C=O);

MS (z/e): 465 (8%), 463 (8%), 384 (100%), 333 (30%), 331 (30%);

Anal. Calcd.: C, 43.99; H, 2.82; N, 3.02%. Found: C, 43.84; H, 2.44; N, 3.07%.

EXAMPLE 6

N-[[6-Methoxy-2-(2,2,2-trifluoroethoxy)-5-(trifluoromethyl)-1-naphthalenyl]carbonyl]-N-(methoxycarbonyl)glycine (I): R$^1$=—O—CH$_2$—CF$_3$; R$^2$=—CH$_3$; X=—OH Step (1) Preparation of N-[[6-Methoxy-2-(2,2,2-trifluoroethoxy)-5-(trifluoromethyl)-1-naphthalenyl]carbonyl]glycine, 1,1-Dimethylethyl Ester 1-Hydroxybenzotriazole (4.27 g, 1.5 eq) and 1-(3-dimethylaminopropyl)-3-ethoxycarbodiimide hydrochloride (4.84 g, 1.2 eq), were added to a stirred solution of 6-methoxy-2-(2,2,2-trifluoroethoxy)-5-(trifluoromethyl)naphthoic acid (7.75 g, 21.0 mmol, prepared by the process of Example 11, Step 3) in anhydrous dimethylformamide (135 mL) under a dry nitrogen atmosphere at room temperature. After 1¼ hours, glycine, t-butyl ester hydrochloride (7.06 g, 2.0 eq) and anhydrous triethylamine (9.68 mL, 3.3 eq) were added. After another 2 hours, the reaction mixture was diluted with water (1.5 L) and extracted with ether (4×200 mL). The extracts were combined and the ether was removed. The crude product was flash chromatographed (7:3 petroleum ether:ethyl acetate, silica) to provide the title compound as a white solid (7.39 g, 73%), m.p. 146°–174.5° C.

NMR (CDCl$_3$, 200 MHz): δ 1.50 (s, 9H, CO$_2$C(CH$_3$)$_3$), 3.97 (s, 3H, ArOCH$_3$), 4.20 (d, 2H, J=5.5 Hz, NHCH$_2$CO$_2$), 4.48 (q, 2H, J=8.3 Hz, OCH$_2$CF$_3$), 6.44 (broad t, 1H, J ~5 Hz, NHCH$_2$), 7.27 (d, 1H, J=9.9 Hz, ArH), 7.37 (d, 1H, J=9.5 Hz, ArH), 8.23 (d, 2H, J=9.2 Hz, 2ArH);

IR (CHCl$_3$, cm$^{-1}$): 3440 (NH), 1736 (C=O), 1662 (CON), 1598 (C=C);

Anal. Calcd.: C, 52.40; H, 4.40; N, 2.91%. Found: C, 52.09; H, 4.43; N, 2.95%.

Step (2) Preparation of N-[[6-Methoxy-2-(2,2,2-trifluoroethoxy)-5-(trifluoromethyl)-1-naphthalenyl]carbonyl]-N-(methoxycarbonyl)glycine, 1,1-Dimethylethyl Ester Sodium hydride (80% by weight dispersion in mineral oil, 381 mg, 1.1 eq) was added to a stirred solution of N-[[6-methoxy-2-(2,2,2-trifluoroethoxy)-5-(trifluoromethyl)-1-naphthalenyl]carbonyl]glycine, 1,1-dimethylethyl ester (5.56 g, 11.5 mmol) in anhydrous THF (90 mL) at room temperature under a dry nitrogen atmosphere. The reaction was heated at 55° C. for 2 hours, then cooled to 0° C. in an ice bath. A solution of methyl chloroformate (1.21 mL, 1.36 eq) in anhydrous THF (30 mL) was slowly added to the 0° C. reaction mixture over 25 minutes. After 10 minutes, the reaction was warmed to room temperature. After 1 hour, the reaction was quenched with saturated aqueous ammonium chloride (1 mL), diluted with ether (100 mL) and preabsorbed onto silica gel. The product was flash chromatographed (4:1 petroleum ether:ethyl acetate, silica)

to provide the title compound as white flakes (4.42 g, 71%), m.p. 53°-54° C.

NMR (CDCl3, 200 MHz): δ 1.53 (s, 9H, CO2C(CH3)3), 3.53 (s, 3H, NCO2CH3), 3.97 (s, 3H, ArOCH3), 4.43 (m, 3H, ArOCH2CF3 and NCH$^1$H$^2$CO2), 4.8 (broad d, 2H, J ~15 Hz, N-CH$^1$H$^2$CO2), 7.23 (d, 1H, J=9.4 Hz, ArH), 7.37 (d, 1H, J=9.5 Hz, ArH), 8.06 (d, 1H, J=9.6 Hz, ArH), 8.26 (d, 1H, J=9.3 Hz, ArH);

IR (CHCl3, cm$^{-1}$): 1745 (2C=O), 1672 (CON), 1600 (C=C);

Anal. Calcd.: C, 51.21; H, 4.30; N, 2.60%. Found: C, 50.94; H, 4.97; N, 2.52%.

Step (3) Preparation of N-[[6-Methoxy-2-(2,2,2-trifluoroethoxy)-5-(trifluoromethyl)-1-naphthalenyl]carbonyl]-N-(methoxycarbonyl)glycine A suspension of N-[[6-methoxy-2-(2,2,2-trifluoroethoxy)-5-(trifluoromethyl)-1-naphthalenyl]carbonyl]-N-(methoxycarbonyl)glycine, 1,1-dimethylethyl ester (5.86 g, 10.9 mmol) in formic acid (135 mL) was stirred at room temperature under a dry nitrogen atmosphere. After 10 minutes, dissolution occurred. After 1 hour, the reaction mixture was diluted with water (1.5 L) and extracted with ether (2×400 mL). The extracts were combined and the ether was removed. The residue was suspended in water (100 mL) and filtered. The solid was washed with water (2×20 mL) and air dried. The crude product was recrystallized from chloroform to provide the title compound as a white powder (4.15 g, 79%), m.p. 186°-187° C.

NMR (DMSO-d$^6$, 400 MHz): δ 3.48 (s, 3H, NCO2CH3), 3.99 (s, 3H, ArOCH3), 4.51 (d, 1H, J=16.4 Hz, NCH$^1$H$^2$CO2H), 4.67 (d, 1H, J=16.9 Hz, NCH$^1$H$^2$CO2H), 4.89 (q, 2H, J=7.8 Hz, ArOCH2CF3), 7.66 (d, 2H, J=9.7 Hz, ArH), 7.99 (d, 1H, J=9.5 Hz, ArH), 8.11 (d, 1H, J=9.5 Hz, ArH);

IR (KBr, cm$^{-1}$): 1771 (C=O), 1746 (C=O), 1682 (C=O), 1612 (C=C);

MS (z/e): 483 (M+, 50%), 351 (94%), 274 (27%), 205 (79%), 134 (100%);

Anal. Calcd.: C, 47.22; H, 3.13; N, 2.90%. Found: C, 47.12; H, 3.44; N, 2.37%.

EXAMPLE 7

N-(Ethoxycarbonyl)-N-[[6-methoxy-2-(2,2,2-trifluoroethoxy)-5-(trifluoromethyl)-1-naphthalenyl]carbonyl]glycine (I): R$^1$=—O—CH2—CF3; R$^2$=—CH2CH3; X=—OH Step (1) Preparation of N-[[6-Methoxy-2-(2,2,2-trifluoroethoxy)-5-(trifluoromethyl)-1-naphthalenyl]carbonyl]carbamic Acid, Ethyl Ester According to the procedure of O. Mitsunobu et al, Bull. Chem. Soc. Japan, 45, 3607 (1972), a solution of 6-methoxy-2-(2,2,2-trifluoroethoxy)-5-trifluoromethyl)-naphthoic acid (4.75 g, 12.9 mmole) and ethoxycarbonyl-t-butylcarbodiimide (2.40 g, 1.10 eq) in anhydrous THF (65 mL) was heated to reflux under a dry nitrogen atmosphere for 2 hours. the reaction was then cooled to room temperature and the THF was removed. The resulting solid was triturated with ether (2×15 mL) to provide the title compound as a beige powder (4.71 g, 83%). A small sample was recrystallized in chloroform:hexane to provide white crystals for analysis, m.p 158°-160° C.

NMR (CDCl3, 200 MHz): δ 1.21 (t, 3H, J=6.8 Hz, CO2CH2CH3), 3.97 (s, 3H, ArOCH3), 4.13 (q, 2H, J=6.9 Hz, NHCO2CH2CH3), 4.48 (q, 2H, J=7.9 Hz, OCH2CF3), 7.25 (d, 1H, J=9.5 Hz, ArH), 7.36 (d, 1H, J=9.5 Hz, ArH), 7.94 (s, 1H, NH), 8.01 (d, 1H, J=9.5 Hz, ArH), 8.30 (d, 1H, J=9.9 Hz, ArH);

IR (CHCl3, cm$^{-1}$): 3395 (NH), 2970 (CH), 1779 and 1766 (C=O), 1694 (C=O), 1605 (C=C);

Anal. Calcd.: C, 49.21; H, 3.44; N, 3.19%. Found: C, 49.47; H, 3.11; N, 3.29%.

Step (2) Preparation of N-(Ethoxycarbonyl)-N-[[6-methoxy-2-(2,2,2-trifluoroethoxy)-5-(trifluoromethyl)-1-naphthalenyl]carbonyl]glycine, 1,1-Dimethylethyl Ester Sodium hydride (80% by weight dispersion in mineral oil, 0.346 g, 1.1 eq) was added to a stirred solution of N-[[6-methoxy-2-(2,2,2-trifluoroethoxy)-5-(trifluoromethyl)-1-naphthalenyl]carbonyl]carbamic acid, ethyl ester (4.60 g, 10.5 mmol) in anhydrous tetrahydrofuran (125 mL) at room temperature under a dry nitrogen atmosphere. After 1 hour, the t-butyl bromoacetate (2.54 mL, 1.5 eq) was added. The reaction was heated to 65° C. for 1 hour, cooled to room temperature, and the THF was removed. The residue was dissolved in ether (200 mL), washed with water (2×50 mL) and saturated aqueous NaCl (1×50 mL). The ether phase was dried with magnesium sulfate and the ether was removed. The crude product was flash chromatographed (17:3 petroleum ether:ethyl acetate, silica) and triturated with petroleum ether to provide the title compound as a white powder (4.60 g, 79%), m.p. 84°-86° C.

NMR (CDCl3, 200 MHz): δ 0.8 (t, 3H, J=7.4 Hz, CO2CH2CH3), 1.53 (s, 9H, CO2C(CH3)3), 3.92 (q, 2H, J=7.6 Hz, CO2CH2CH3), 3.97 (s, 3H, ArOCH3), 4.42 (q, 2H, J=7.9 Hz, OCH2CF3), 4.85 (d, 2H, J=17.5 Hz, NCH2CO2), 7.23 (d, 1H, J=9.5 Hz, ArH), 7.38 (d, 1H, J=9.2 Hz, ArH), 8.08 (d, 1H, J=9.5 Hz, ArH), 8.24 (d, 1H, J=8.7 Hz, ArH);

IR (CHCl3, cm$^{-1}$): 2995 (CH), 1744 (2C=O), 1678 (C=O), 1604 (C=C);

Anal. Calcd.: C, 52.08; H, 4.55; N, 2.53%. Found: C, 52.02; H, 4.24; N, 2.54%.

Step (3) Preparation of N-(Ethoxycarbonyl)-N-[[6-methoxy-2-(2,2,2-trifluoroethoxy)-5-(trifluoromethyl)-1-naphthalenyl]carbonyl]glycine A suspension of N-(ethoxycarbonyl-N-[[6-methoxy-2-(2,2,2-trifluoroethoxy)-5-trifluoromethyl)-1-naphthalenyl]carbonyl]glycine, 1,1-dimethylethyl ester (4.50 g, 8.13 mmol) in formic acid (140 mL) was stirred at room temperature under a dry nitrogen atmosphere. After 10 minutes, dissolution occurred. After 1 hour, the reaction was diluted with water (1.3 L) and stirred rapidly for 5 minutes. The resultant oil was extracted with ether (2×150 mL). The extracts were combined and the ether was removed. The residue was suspended in water (50 mL) and filtered. The solid was washed with water (2×30 mL) and dried for 30 minutes. The crude product was then recrystallized from chloroform:petroleum ether to provide the title compound as white crystals (2.06 g, 51%), m.p. 165.5°-167° C.

NMR (DMSO-d$^6$, 400 MHz): δ 0.65 (t, 3H, J=7.1 Hz, CO2CH2CH3), 3.84 (q, 2H, J=7.1 Hz, CO2CH2CH3), 3.99 (s, 3H, ArOCH3), 4.50 (d, 1H, J=17.0 Hz, NCH$^1$H$^2$CO2H), 4.65 (d, 1H, J=17.5 Hz, NCH$^1$H$^2$CO2H), 4.89 (dq, 2H, J=8.8 and 2.3 Hz, OCH2CF3), 7.66 (d, 1H, J=9.8 Hz, ArH), 7.67 (d, 1H, J=9.5 Hz, ArH), 8.01 (d, 1H, J=9.5 Hz, ArH), 8.12 (dd, 1H, J=9.7 and 1.2 Hz, ArH);

IR (KBr, cm$^{-1}$): 1749 (C=O), 1731 (C=O), 1677 (C=O), 1602 (C=C);

MS (z/e): 497 (37%), 351 (63%), 86 (100%);
Anal. Calcd.: C, 48.30; H, 3,44; N, 2.82%. Found: C, 48.34; H, 3.83; N, 2.74%.

EXAMPLE 8

N-[[2-Chloro-6-methoxy-5-(trifluoromethyl)-1-naphthalenyl]carbonyl]-N-(ethoxycarbonyl)glycine (I): $R^1$=—Cl; $R^2$=—$CH_2CH_3$; X=—OH Step (1) Preparation of N-[[2-Chloro-6-methoxy-5-(trifluoromethyl)-1-naphthalenyl]carbonyl]carbamic Acid, Ethyl Ester A solution of 2-chloro-6-methoxy-5-(trifluoromethyl)naphthoic acid (3.50 g, 11.5 mmol, prepared by the process of Example 14), and ethoxycarbonyl-t-butylcarbodiimide (2.2 g, 1.1 eq) in dry tetrahydrofuran (58 mL) was heated to reflux under a dry nitrogen atmosphere for 5½ hours. The tetrahydrofuran was removed and the resultant solid was triturated with ether (2×15 mL) and dried in vacuo. A second crop was recovered from the ether and combined with the product (3.36 g, 78%). The small sample was further purified by flash chromatography (70/30 petroleum ether/ethyl acetate) to provide the analytically pure product as a white solid, m.p. 169°–171° C.

NMR ($CDCl_3$, 200 MHz): δ 1.18 (t, 3H, J=7 Hz, $CH_2CH_3$), 3.99 (s, 3H, $OCH_3$), 4.12 (q, 2H, J=7 Hz, $CH_2CH_3$), 7.37 (d, 1H, J=10 Hz, ArH), 7.51 (d, 1H, J=10 Hz, ArH), 7.90 (d, 2H, ArH, NH), 8.21 (d, 1H, J=10 Hz, ArH);

IR ($CHCl_3$, $cm^{-1}$): 3400 (NH), 1765 (C=O), 1690 (C=O), 1615 and 1585 (C=C);

Anal. Calcd.: C, 51.15; H, 3.49; N, 3.73%. Found: C, 51.08; 1 H, 3.51; N, 3.46%.

Step (2) Preparation of N-[[2-Chloro-6-methoxy-5-(trifluoromethyl)-1-naphthalenyl]carbonyl]-N-(ethoxycarbonyl)glycine, 1,1-Dimethylethyl Ester Sodium hydride (0.281 g of 80% by weight dispersion in mineral oil, 1.1 eq) was added to a solution of N-[[2-chloro-6-methoxy-5-trifluoromethyl-1-naphthalenyl]carbonyl]carbamic acid, ethyl ester (3.20 g, 8.52 mmol) in dry tetrahydrofuran (100 mL) under a dry nitrogen atmosphere at room temperature. After stirring for 1 hour, t-butyl bromoacetate (2.06 mL, 1.5 eq) was added. The reaction mixture was stirred for 25 minutes at room temperature, heated to 65° C. for one hour, and cooled back to room temperature. The solvent was removed and the residue was dissolved in ether (200 mL), washed with water (2×50 mL) and saturated aqueous NaCl (1×50 mL), dried over magnesium sulfate, filtered and combined with silica gel. The ether was removed and the absorbate was flash chromatographed (93/7 petroleum ether/ethyl acetate) to give the product as a white solid (3.58 g, 86%). A small portion was triturated with petroleum ether and dried overnight in vacuo at 40° C. to give the analytical sample, m.p. 107°–108° C.

NMR ($CDCl_3$, 200 MHz): δ 0.77 (t, 3H, J=7 Hz, $OCH_2CH_3$), 1.55 (s, 9H, $C(CH_3)_3$), 3.93 (q, 2H, J=6 Hz, $OCH_2CH_3$), 3.99 (s, 3H, $ArOCH_3$), 4.51 (d, 1H, J=18 Hz, $NCH^1H^2$), 4.84 (d, 1H, J=17 Hz, $NCH^1H^2$), 7.40 (d, 1H, J=10 Hz, ArH), 7.47 (d, 1H, J=10 Hz, ArH), 8.15 (m, 2H, ArH);

IR ($CHCl_3$, $cm^{-1}$): 1750–1730 (C=O), 1675 (C=O);
Anal. Calcd.; C, 53.94; H, 4.73; N, 2.86%. Found: C, 53.57; H, 4.52; N, 2.83%.

(3) Preparation of N-[[2-Chloro-6-methoxy-5-(trifluoromethyl)-1-naphthalenyl]carbonyl]-N-(ethoxycarbonyl)glycine A suspension of N-[[2-chloro-6-methoxy-5-(trifluoromethyl)-1-naphthalenyl]carbonyl]-N-(ethoxycarbonyl)glycine, 1,1-dimethylethyl ester (3.13 g, 6.39 mmol) in formic acid (120 mL) was stirred for 3 hours at room temperature under a dry nitrogen atmosphere. Dissolution occurred after an hour. The reaction mixture was diluted with water (1.5 L) and extracted with ether. The extracts were combined, washed well with water and concentrated to leave an oil. The oil was diluted with water and extracted with chloroform. The extracts were combined, dried over magnesium sulfate, filtered and concentrated. The crude solid was recrystallized from benzene:petroleum ether and dried overnight at 90° C. in vacuo to give the title compound as a white solid (2.31 g, 85%), m.p. 144°–146° C.

NMR ($CDCl_3$, 400 MHz): δ 0.78 (t, 3H, J=7 Hz, —$CH_2CH_3$), 3.97 (q, 2H, J=7 Hz, $CH_2CH_3$), 4.00 (s, 3H, $OCH_3$), 4.79 (d, 1H, J=17 Hz, $NCH^1H^2$), 5.00 (d, 1H, J=17 Hz, $NCH^1H^2$), 7.39 (d, 1H, J=9 Hz, ArH), 7.50 (d, 1H, J=9 Hz, ArH), 8.02 (d, 1H, J=9 Hz, ArH), 8.20 (d, 1H, J=9 Hz, ArH);

IR (KBr, $cm^{-1}$): 3200–2800 (COOH), 1765 (C=O), 1735 (C=O), 1690 (C=O);

MS (CI): 434 (m+H) (76%), 414 (36%), 309 (80%), 287 (100%), 253 (58%), 187 (54%);

Anal. Calcd.: C, 49.84; H, 3.48; N, 3.23%. Found: C, 49.68; H, 3.36; N, 3.18%.

EXAMPLE 9

N-[[2-Bromo-6-methoxy-5-(trifluoromethyl)-1-naphthalenyl]carbonyl]-N-(ethoxycarbonyl)glycine (I): $R^1$=—Br; $R^2$=—$CH_2CH_3$; X=—OH Step (1) Preparation of 2-Bromo-N-(ethoxycarbonyl)-6-methoxy-5-(trifluoromethyl)-1-naphthalenecarboxamide According to the procedure of O. Mitsunobu et al, Bull. Chem. Soc., Japan, 45, 3607 (1972), a solution of 2-bromo-6-methoxy-5-trifluoromethyl-1-naphthoic acid (4.50 g, 12.9 mmol, prepared by the process of Step 2, Example (11), and ethoxycarbonyl-t-butylcarbodiimide (2.40 g, 14.1 mmol) in dry tetrahydrofuran (80 mL) was heated to reflux under a dry nitrogen atmosphere for 2⅓ hours. The THF was removed and the residue was dissolved in chloroform and the solvent evaporated. The resultant solid was triturated with ether (2×5 mL) and dried in vacuo to provide the title compound as an off white solid (4.61 g, 85%), m.p. 169°–171° C.

NMR ($CDCl_3$, 200 MHz): δ 1.18 (t, 3H, J=6.9 Hz, $CO_2CH_2CH_3$), 3.99 (s, 3H, $ArOCH_3$), 4.12 (q, 2H, J=6.9 Hz, $CO_2CH_2CH_3$), 7.35 (d, 1H, J=9.1 Hz, ArH), 7.65 (d, 1H, J=9.5 Hz, ArH), 7.87 (s, 1H, NH), 7.90 (d, 1H, J=9.6 Hz, ArH), 8.13 (d, 1H, J=9.6 Hz, ArH);

IR ($CHCl_3$, $cm^{-1}$): 3400 (NH), 1765 (C=O), 1692 (C=O), 1616 and 1582 (C=C);

Anal. Calcd.: C, 45.73; H, 3.12; N, 3.33%. Found: C, 45.68; H, 3.50; N, 3.21%.

Step (2) Preparation of N-[[2-Bromo-6-methoxy-5-(trifluoromethyl)-1-naphthalenyl]carbonyl]-N-(ethoxycarbonyl)glycine, 1,1-Dimethylethyl Ester Sodium hydride (80% by weight dispersion in mineral oil, 0.347 g, 1.1 eq) was added to a stirred solution of 2-bromo-N-(ethoxycarbonyl)-6-methoxy-5-(trifluoromethyl)-1-naphthalenecarboxamide (4.41 g, 10.5 mmol) in anhydrous tetrahydrofuran (150 mL) at room temperature under a dry nitrogen atmosphere. After 1 hour, the t-butyl bromoacetate (2.54 mL, 1.5 eq) was added and the reaction was heated to 55° C. After 1½ hours of heating, the reaction was cooled to room temperature and the THF was removed. The residue was suspended in ether (250 mL), washed with water (2×100 mL) and saturated aqueous NaCl (1×50 mL), dried with magnesium sulfate, and the ether was removed. The resultant oil was triturated with petroleum ether (1×50 mL) to provide the title compound as a white powder (4.78 g, 85%). A small samle was recrystallized in ether-petroleum ether to provide white crystals for analysis, m.p. 109.5°–112° C.

NMR (CDCl$_3$, 200 MHz): δ 0.75 (t, 3H, J=6.8 Hz, CO$_2$CH$_2$CH$_3$), 1.54 (s, 9H, CO$_2$C(CH$_3$)$_3$), 3.91 (q, 2H, J=7.0 Hz, CO$_2$CH$_2$CH$_3$), 3.98 (s, 3H, ArOCH$_3$), 4.50 (d, 1H, J=17.2 Hz, NCH$^1$H$^2$CO$_2$), 4.83 (d, 1H, J=16.6 Hz, NCH$^1$H$^2$CO$_2$), 7.38 (d, 1H, J=9.2 Hz, ArH), 7.60 (d, 1H, J=9.6 Hz, ArH), 8.11 (dd, 2H, J=11.0 and 9.8 Hz, ArH);

IR (CHCl$_3$, cm$^{-1}$): 2975 (CH), 1732 (C=O), 1672 (C=O), 1610 and 1578 (C=C)

Anal. Calcd.: C, 49.45; H, 4.34; N, 2.62%. Found: C, 49.69; H, 4.36; N, 2.75%.

Step (3) Preparation of N-[[2-Bromo-6-methoxy-5-(trifluoromethyl)-naphthalenyl]carbonyl]-N-(ethoxycarbonyl)glycine A suspension of N-[[2-bromo-6-methoxy-5-(trifluoromethyl)-1-naphthalenyl]carbonyl]-N-(ethoxycarbonyl)glycine, 1,1-dimethylethyl ester (4.68 g, 8.76 mmol) in formic acid (150 mL) was stirred at room temperature under a dry nitrogen atmosphere. After 15 minutes, dissolution occurred. After 1¼ hours, the reaction was diluted with water (1.2 L). The aqueous phase was extracted with ether (2×300 mL). The extracts were combined, dried with magnesium sulfate, and the ether was removed. The residue was suspended in water (150 mL) and filtered. The solid was washed with water (2×30 mL) and dried. The crude product was recrystallized in chloroform:hexane twice to yield the title compound as white needles (2.24 g, 53%), m.p. 167°–168.5° C.

NMR (d$^6$DMSO, 400 MHz): δ 0.69 (t, 3H, J=7.1 Hz, CO$_2$CH$_2$CH$_3$), 3.87 (t, 2H, J=7.1 Hz, CO$_2$CH$_2$CH$_3$), 4.02 (s, 3H, ArOCH$_3$), 4.59 (d, 1H, J=19.9 Hz, NCH$^1$H$^2$CO$_2$H), 4.71 (d, 1H, J=17.4 Hz, NCH$^1$H$^2$CO$_2$H), 7.71 (d, 1H, J=9.5 Hz, ArH), 7.82 (d, 1H, J=9.4 Hz, ArH), 8.01 (d, 1H, J=9.3 Hz, ArH), 8.15 (d, 1H, J=9.5 Hz, ArH);

IR (KBr, cm$^{-1}$): 1761 (C=O), 1738 (C=O), 1690 (C=O), 1620 and 1589 (C=C);

MS (z/e): 479 (2.4%), 477 (2.6%), 398 (46%), 352 (20%), 333 (25%), 331 (25%), 324 (100%), 269 (51%);

Anal. Calcd.: C, 45.21; H, 3.16; N, 2.93%. Found: C, 45.36; H, 2.89; N, 2.87%.

EXAMPLE 10

2-Fluoro-6-methoxy-5-(trifluoromethyl)-1-naphthoic Acid (II): R$^1$=—F

Step (1) Preparation of 1-Bromomethyl-2-fluoro-6-methoxy-5-(trifluoromethyl)naphthalene A suspension of N-bromosuccinimide (6.93 g, 1.1 eq), benzoyl peroxide (38 mg) and 2-fluoro-6-methoxy-1-methyl-5-(trifluoromethyl)naphthalene (9.14 g, 35.39 mmol) in carbontetrachloride (160 mL) was heated to reflux with stirring under a dry nitrogen atmosphere for 1.5 hours. The reaction mixture was cooled to room temperature and filtered. The solid was washed with carbon tetrachloride (3×30 mL). The solvent was removed from the combined CCl$_4$ phases to provide the product as a white solid in quantitative yield. A small portion of this solid was recrystallized from hexane:ethylacetate, m.p. 97°–100° C.

NMR (CDCl$_3$, 200 MHz): δ 4.01 (s, 3H, OCH$_3$), 4.94 (d, 2H, J=1.5 Hz, CH$_2$Br), 7.32 (t, 1H, J=9.4 Hz, ArH), 7.49 (d, 1H, J=9.5 Hz, ArH), 8.25 (m, 1H, ArH), 8.25 (d, 1H, ArH);

IR (CHCl$_3$, cm$^{-1}$): 1615 (aromatic C—C)

Anal. Calcd.: C, 46.32; H, 2.69%. Found: C, 46.04; H, 2.34%.

Step (2) Preparation of 2-Fluoro-1-hydroxymethyl-6-methoxy-5-(trifluoromethyl)naphthalene A suspension of 1-bromomethyl-2-fluoro-6-methoxy-5-(trifluoromethyl)naphthalene (11.16 g, 35 mmol), sodium formate (5.85 g, 86 mmol), ethanol (134 mL) and water (34 mL) was heated to reflux with stirring. Dissolution occurred with 20 minutes. After 1.5 hours the heating source was removed, 2.5N NaOH (14mL) was added, and the reaction mixture was cooled to room temperature. The ethanol was removed, water (100 mL) was added and the solid was filtered. The white solid was washed with water and dried in vacuo to give the product in quantitative yield. A small portion was recrystallized from petroleum ether:ethyl acetate, m.p. 113°–114° C.

NMR (CDCl$_3$, 200 MHz): δ 1.74 (t, 1H, J=6.2 Hz, —OH), 3.99 (s, 3H, OCH$_3$), 5.15 (dd, 2H, J=1.3 and 6.2 Hz, —CH$_2$OH), 7.32 (t, 1H, J=9.4 Hz, ArH), 7.42 (d, 1H, J=9.4 Hz, ArH), 8.18 (m, 1H, ArH), 8.41 (d, 1H, J=9.4 Hz, ArH);

IR (CHCl$_3$, cm$^{-1}$): 3610, 3420 (OH), 1615 (aromatic C—C);

Anal. Calcd.: C, 56.94; H, 3.67%.

Found: C, 56.71; H, 3.86%.

Step (3) Preparation of 2-Fluoro-6-methoxy-5-(trifluoromethyl)-1-naphthoic Acid

Jones reagent (2.67M in CrO$_3$, 25 mL, 66.8 mmol) was added dropwise over a 5 minute period to a mechanically stirred, cold (0°–10° C.) solution of 2-fluoro-1-hydroxymethyl-6-methoxy-5-(trifluoromethyl)naphthalene (11.59 g, 34.6 mmol) in acetone (120 mL). The reaction mixture was warmed to room temperature and after 2 hours it was quenched with isopropanol. The reaction mixture was diluted with ether to a volume of ~500 mL and then filtered through celite. The celite was washed with more ether. The ether was removed and the resildue was dissolved in 5% NaOH (100 mL). An additional 100 mL of water was added and this aqueous phase was extracted with ether (4×200 mL), ethyl acetate (1×100 mL) and CH$_2$Cl$_2$ (1×200 mL). These extracts were discarded. The base phase was acidified to pH 1–3 with 10% HCl and the tan solid was collected and dried in vacuo (7.3 g, 73%). A small sample was recrystallized from ethanol:water, m.p. 179°–181° C.

NMR (CDCl$_3$, 200 MHz): δ 4.02 (s, 3H, OCH$_3$), 7.40 (t, 1H, J=9.5 Hz, ArH), 7.46 (d, 1H, J=9.6 Hz, ArH), 8.37 (m, 1H, ArH), 8.53 (d, 1H, J=9.6 Hz, ArH);

IR (KBr, cm$^{-1}$): 3600–2500 (CO$_2$H), 1695 (CO$_2$H)

Exact Mass: Calcd.=288.0409; Found=288.0380

EXAMPLE 11

6-Methoxy-2-(2,2,2-trifluoroethoxy)-5-(trifluoromethyl)naphthoic Acid (II): R$^1$=—O—CH$_2$—CF$_3$ Step (1) Preparation of (2-Bromo-6-methoxy-5-trifluoromethyl-1-naphthalenyl)methanol According to the procedure of E. L. Eliel et al, J. Chem. Soc. 1628 (1955), sodium formate (12.88 g, 2.4 eq) and water (42 mL) were added to a stirred suspension of 2-bromo-1-bromomethyl-6-methoxy-5-trifluoromethylnaphthalene (32.4 g, 78.0 mmol, prepared by the process of Example 13) in ethanol (160 mL) at room temperature. The suspension was heated to reflux and after 1 hour, more sodium formate (1.07 g, 0.2 eq) was added. After 10¾ hours, water (25 mL) was added and the ethanol was removed by distillation. The reaction was cooled to room temperature and basified to pH9 with 10% aqueous sodium hydroxide solution. The basic suspension was diluted with water (1.5 L) and filtered. The solid was washed with water (2×30 mL) then triturated with chloroform (2×25 mL) and dried to provide the light yellow solid (23.10 g, 87%). A small sample was flash chromatographed (7:3 to 3:2 petroleum ether:ethyl acetate eluant gradient, silica), to provide a white solid for analysis, m.p. 171°–173° C.

NMR (d$^6$DMSO, 200 MHz): δ 4.01 (s, 3H, ArOCH$_3$), 5.07 (d, 2H, J=4.4 Hz, CH$_2$OH), 5.44 (t, 1H, J=5.2 Hz, CH$_2$OH), 7.70 (d, 1H, J=9.5 Hz, ArH), 7.78 (d, 1H, J=9.1 Hz, ArH), 7.90 (d, 1H, J=9.9 Hz, ArH), 8.56 (d, 1H, J=10.2 Hz, ArH);

IR (KBr, cm$^{-1}$): 3318 (OH), 1613 and 1588 (C=C);

Anal. Calcd.: C, 46.59; H, 3.01%. Found: C, 46.77; H, 3.36%.

Step (2) Preparation of 2-Bromo-6-methoxy-5-trifluoromethyl-1-naphthoic Acid

Jones reagent (2.67M in CrO$_3$, 34 mL, 1.32 eq) was added slowly to a stirred solution of (2-bromo-6-methoxy-5-trifluoromethyl-1-naphthalenyl)methanol (23.10 g, 68.9 mmol) in acetone (450 mL) at 0° C. After 5 minutes, the reaction was warmed to room temperature. After 1 hour, more Jones reagent (6.8 mL, 0.26 eq) was added. After 2½ hours, the reaction was quenched with isopropanol (10 mL) and diluted with water (1.4 L). The aqueous phase was extracted with ethyl acetate (3×400 mL). The extracts were combined and the ethyl acetate phase was quickly extracted with 5N sodium hydroxide solution (3×350 mL). The base extracts were combined and acidified to pH1 with concentrated hydrochloric acid. The aqueous acid suspension was stirred overnight at room temperature. The solid was collected by suction filtration, washed with water (1×25 mL), and dried to provide the light yellow solid (16.05 g, 67%), m.p. 221°–222.5° C.

NMR (d$^6$DMSO, 400 MHz): δ 4.02 (s, 3H, ArOCH$_3$), 7.77 (d, 1H, J=9.7 Hz, ArH), 7.84 (d, 1H, J=9.4 Hz, ArH), 8.02 (d, 2H, J=9.3 Hz, ArH);

IR (KBr, cm$^{-1}$): 1710 (C=O), 1612 and 1583 (C=C);

MS (z/e): 350 (99%), 348 (100%), 333 (20%), 331 (20%), 307 (24%), 305 (26%);

Anal. Calcd.: C, 44.73; H, 2.31%.
Found: C, 44.69; H, 2.38%.

Step (3) Preparation of 6-Methoxy-2-(2,2,2-trifluoroethoxy)-5-(trifluoromethyl)naphthoic Acid 2,2,2-Trifluoroethanol (8.35 mL, 4.0 eq) was added slowly to a suspension of sodium hydride (60% by weight dispersion in mineral oil, 7.68 g, 6.7 eq) in anhydrous hexamethylphosphoramide (85 mL) at room temperature contained in a flame dried reaction vessel under argon. After 20 minutes, 2-bromo-6-methoxy-5-trifluoromethyl-1-naphthoic acid (10.00 g, 28.6 mmol) and copper (I) iodide (10.91 g, 2.0 eq) were added with caution. After 50 minutes, the reaction was heated to 65° C. for 1½ hours, then cooled to room temperature. The reaction was diluted with water (800 mL) and acidified to pH1 with concentrated hydrochloric acid. The acid phase and ethyl acetate (200 mL) were stirred together for 15 minutes then filtered through celite; the celite was washed with more ethyl acetate (2×100 mL). The two layers of the filtrate were separated. The aqueous layer was extracted with ethyl acetate (2×150 mL). All the ethyl acetate phases were combined and the ethyl acetate was removed. The residue was dissolved in 0.5N sodium hydroxide (800 mL) and extracted with ether (2×150). The extracts were discarded. The base phase was acidified to pH1 with concentrated hydrochloric acid. The acid phase was extracted with ether (3×200 mL). The extracts were combined, washed with saturated aqueous sodium chloride (1×50 mL), dried with magnesium sulfate, and the ether was removed to provide the light yellow solid (9.33 g, 88%). A small sample was recrystallized in ethanol:water for analysis, m.p. 190°–192° C.

NMR (d$^6$DMSO, 200 MHz): δ 3.99 (s, 3H, ArOCH$_3$), 4.93 (q, 2H, J=8.9 Hz, OCH$_2$CF$_3$), 7.71 (2d, 2H, J=4.4 and 9.4 Hz, ArH), 8.00 (d, 1H, J=9.5 Hz, ArH), 8.13 (d, 1H, J=8.4 Hz, ArH);

IR (KBr, cm$^{-1}$): 1718 (C=O), 1614 (C=C);

Anal. Calcd.: C, 48.93; H, 2.74%. Found: C, 48.90; H, 3.13%.

EXAMPLE 12

Step (1) Preparation of 1-Bromomethyl-2-chloro-6-methoxy-5-trifluoromethylnaphthalene N-Bromosuccinimide (11.62 g, 1.1 eq) and benzoylperoxide (0.061 g, 0.0044 eq) were added to a stirred solution of 2-chloro-6-methoxy-1-methyl-5-trifluoromethylnaphthalene (16.3 g, 0.0593 mol, prepared by the process of Example 14, Step 2) in carbon tetrachloride (200 mL) at room temperature, under a dry nitrogen atmosphere. The reaction was heated to reflux for 29 hours with additional N-bromosuccinamide (10.55 g, 1 eq) and benzoylperoxide (0.035 g, 0.0025 eq) added after 5¼ hours. The reaction mixture was cooled to room temperature and filtered. The solid was washed with hot carbon tetrachloride. The filtrate was concentrated to provide the white solid product (21.88 g, 100%). A small sample was purified by flash chromatography (4/1 petroleum ether/chloroform) to give analytical sample, m.p. 127°–130° C.

NMR (CDCl$_3$, 200 MHz): δ 4.01 (s, 3H, OCH$_3$), 5.05 (s, 2H, CH$_2$Br), 7.46 (d, 1H, J=8 Hz, ArH), 7.50 (d, 1H, J=7 Hz, ArH), 8.13 (d, 1H, J=8 Hz, ArH), 8.26 (d, 1H, J=10 Hz, ArH);

IR (CHCl$_3$, cm$^{-1}$): 1610 and 1580 (C=C);

Anal. Calcd.: C, 44.16; H, 2.56%. Found: C, 44.13; H, 2.46%.

Step (2) Preparation of 2-Chloro-1-hydroxymethyl-6-methoxy-5-trifluoromethylnaphthalene Sodium formate (9.68 g, 2.4 eq) and water (57 mL) were added to a stirred suspension of 1-bromomethyl-2-chloro-6-methoxy-5-trifluoromethylnaphthalene (20.97 g, 0.0593 mol) in ethanol (226 mL) at room temperature. The reaction mixture was heated to reflux for 3½ hours. The heat was removed and 2.5N sodium hydroxide (27 mL, 1 eq) was added to the stirred hot mixture. The ethanol was removed and the residue was diluted with water (~100 mL). The aqueous suspension was filtered. The solid was washed with water and dried in vacuo to provide the off white solid product (16.01 g, 93%). A small sample was purified by flash chromatography (3/2 petroleum ether:ethyl acetate) to give an analytical sample, m.p. 162°–166° C.

NMR (CDCl$_3$, 200 MHz): δ 1.86 (t, 1H, J=5 Hz, —CH$_2$OH), 4.04 (s, 3H, OCH$_3$), 5.29 (d, 2H, J=5 Hz, CH$_2$OH), 7.44 (d, 1H, J=10 Hz, ArH), 7.53 (d, 1H, J=10 Hz, ArH), 8.16 (d, 1H, J=10 Hz, ArH), 8.46 (d, 1H, J=10 Hz, ArH);

IR (KBr, cm$^{-1}$): 3290 (—OH), 1608 (C=C);

Anal. Calcd.: C, 53,90; H, 3.13%. Found: C, 53.81; H, 3.36%.

Step (3) Preparation of 2-Chloro-6-methoxy-5-trifluoromethyl)naphthoic Acid

Jones reagent (2.67M in CrO$_3$, 27 mL, 1.34 eq) was added to a mechanically stirred solution of 2-chloro-1-hydroxymethyl-6-methoxy-5-trifluoromethylnaphthalene (15.61 g, 0.0537 mol) in acetone (324 mL) at 0° C. The reaction mixture was warmed to room temperature and stirred for 4 hours with another 10 mL (0.50 eq) of Jones reagent added after 2 hours. The reaction was quenched with isopropanol (~250 mL), diluted with ether (~1 L), and filtered through celite. The filtrate was concentrated and the residue was dissolved in 5% NaOH (150 mL). The aqueous phase was extracted with ether (1 L) and methylene chloride (500 mL). The extracts were discarded. The aqueous phase was acidified to pH1 with 10% hydrochloric acid. The solid precipitate was filtered, washed with water and dried in vacuo at 80° C. to give the product as a white solid (10.98 g, 67%). A small portion was recrystallized from chloroform/petroleum ether to give the analytical sample, m.p. 214° C. (dec.).

NMR (d$^6$DMSO, 200 MHz): δ 4.02 (s, 3H, OCH$_3$), 7.75 (t, 2H, J=10 Hz, ArH), 8.03 (d, 1H, J=10 Hz, ArH), 8.11 (d, 1H, J=10 Hz, ArH);

IR (KBr, cm$^{-1}$): 3600-2500 (CO$_2$H), 1687 (C=O);

Anal. Calcd.: C, 51.25; H, 2.65%. Found: C, 50.89; H, 2.84%.

EXAMPLE 13

Preparation of 2-Bromo-1-bromomethyl-6-methoxy-5-trifluoromethylnaphthalene

N-Bromosuccinimide (21.07 g, 1.5 eq) and benzoyl peroxide (84 mg, 0.0044 eq) were added to a stirred solution of 2-bromo-6-methoxy-1-methyl-5-trifluoromethylnaphthalene (25.19 g, 78.9 mmol, prepared by the process of Example 14, Step (1) in carbon tetrachloride (300 mL) at room temperature under a dry nitrogen atmosphere. The reaction was heated to reflux for 6 hours, then cooled to ~50° C. The warm reaction mixture was filtered. The solid washed with warm carbon tetrachloride (2×30 mL). The carbon tetrachloride was removed from the filtrate to provide the light yellow solid (32.4 g, 100%), m.p. 141.5°-143° C.

NMR (CDCl$_3$, 200 MHz): δ 4.02 (s, 3H, OCH$_3$), 5.09 (s, 2H, CH$_2$br), 7.46 (d, 1H, J=9.5 Hz, ArH), 7.66 (d, 1H, J=9.5 Hz, ArH), 8.06 (dm, 1H, ArH), 8.30 (d, 1H, J=9.5 Hz, ArH);

IR (CHCl$_3$, cm$^{-1}$): 1615, 1585 (ArC—C);

Anal. Calcd.: C, 39.23; H, 2.28%. Found: C, 38.90; H, 2.41%.

EXAMPLE 14

Step (1) Preparation of 2-Bromo-6-methoxy-1-methyl-5-trifluoromethylnaphthalene

A solution of bromine (6.41 mL, 0.125 mol) in glacial acetic acid (28 mL) was added to a stirred solution of 2-methoxy-5-methyl-1-trifluoromethylnaphthalene (20.9 g, 0.083 mmol) in glacial acetic acid (300 mL) over a 25 minute period. The solution was stirred at room temperature for 22 hours. The reaction mixture was poured into dilute aqueous NaHSO$_3$ (2 L). The yellow solid product was collected via suction filtration and dried in vacuo (26.2 g, 98%), m.p. 98°-100.5° C.

NMR (CDCl$_3$, 200 MHz): δ 2.77 (s, 3H, CH$_3$), 3.99 (s, 3H, OCH$_3$), 7.33 (d, 1H, J=9.5 Hz, ArH), 7.63 (d, 1H, J=9.6 Hz, ArH), 7.91 (dm, 1H, ArH), 8.19 (d, 1H, J=9.5 Hz, ArH);

IR (CHCl$_3$, cm$^{-1}$): 1610 (ArC—C);

Anal. Calcd.: C, 48.93; H, 3.16%. Found: C, 48.57; H, 3.38 %.

Step (2) Preparation of 2-Chloro-6-methoxy-1-methyl-5-trifluoromethylnaphthalene Copper (I) chloride (35.78 g, 6 eq) was added to a solution of 2-bromo-6-methoxy-1-methyl-5-trifluoromethylnaphthalene (19.22 g, 0.0602 mol) in dry DMSO (194 mL) at room temperature under a nitrogen atmosphere. The reaction mixture was heated at ~188° C. for 3 hours, then cooled to room temperature and diluted with water (3 L). The resultant solids were collected and triturated well with ethyl acetate (2 L total). The triturates were combined, dried over magnesium sulfate, filtered, and the solvent removed to give the desired product as a white solid (16.7 g, 100%). A small sample was purified by flash chromatography (eluant 90/10 petroleum ether/chloroform) to give an analytically pure product, m.p. 102°-103° C.

NMR (CDCl$_3$, 200 MHz): δ 2.72 (s, 3H, —CH$_3$), 3.99 (s, 3H, OCH$_3$), 7.34 (d, 1H, J=10 Hz, ArH), 7.48 (d, 1H, J=10 Hz, ArH), 7.98 (d, 1H, J=9 Hz, ArH), 8.17 (d, 1H, J=10 Hz, ArH);

IR (CHCl$_3$, cm$^{-1}$): 2950 and 2858 (CH), 1610 and 1590 (C=C);

Anal. Calcd.: C, 56.85; H, 3.67%. Found: C, 56.57; H, 3.95%.

EXAMPLE 15

2-Fluoro-6-methoxy-1-methyl-5-(trifluoromethyl)naphthalene

Step (1) Preparation of 2-Methoxy-5-methyl-6-nitro-1-(trifluoromethyl)naphthalene To a cooled solution (3° to 4° C.) of acetic anhydride (640 mL) was added fuming nitric acid (90%, specific gravity=1.5, 160 mL) dropwise via an addition funnel at such a rate as to keep the internal temperature at or below 8° C. (~1 hour 20 minutes total addition time). After the internal temperature had again cooled to 3°-4° C., 2-methoxy-5-methyl-1-trifluoromethylnaphthalene (200 g, 0.833 mol) was added portion wise. The portions added were small enough such that the internal temperature did not rise above 10° C. and each portion was added when the temperature had cooled to 5° C. (addition time ~1 hour 15 minutes). After an additional 15 minutes the reaction mixture was added to water (3 L). The resulting amorphous solid was filtered, washed with water and the lumps broken up and dried in vacuo overnight. The dry solid (~225 g) was recrystallized from 95:5 ethanol:isopropanol (3 L). The resulting long yellow needles were filtered and washed with ethanol (2×50 mL) to provide the product (97.5 g, 41%), m.p. 141°-142° C.

NMR (CDCl$_3$, 200 MHz): δ 2.84 (s, 3H, CH$_3$), 4.05 (s, 3H, OCH$_3$), 7.47 (d, 1H, J=10.0 Hz, ArH), 7.87 (d, 1H, J=9.9 Hz, ArH), 8.16 (dm, 1H, ArH), 8.39 (d, 1H, J=10.0 Hz, ArH);

IR (CHCl$_3$, cm$^{-1}$); 1615 (aromatic C=C);

MS (z/e): 285 (67%), 268 (80%), 266 (13%), 248 (48%), 240 (42%), 196 (100%), 146 (100%);

Anal. Calcd.: C, 60.47; H, 3.90%. Found: C, 60.28; H, 3.80%.

Step (2) Preparation of 6-Amino-2-methoxy-5-methyl-1-trifluoromethylnaphthalene

A suspension of 2-methoxy-5-methyl-6-nitro-1-trifluoromethylnaphalene (16.5 g, 57.85 mmol), 10% palladium on carbon (1.69 g) in absolute ethanol (900 mL) was hydrogenated at 40 psi H₂ pressure at room temperature for 2 hours. The reaction mixture was then filtered through sulkafloc and the sulkafloc was washed with fresh ethanol. The ethanol was then removed from the filtrate to provide the product as a yellow solid (14.3 g, 97%), m.p. 109°–110° C.

NMR (CDCl₃, 200 MHz): δ 2.40 (s, 3H, CH₃), 3.77 (broad s, 2H, NH₂), 3.95 (s, 3H, OCH₃), 7.04 (d, 1H, J=9.7 Hz, ArH), 7.26 (d, 1H, J=9.5 Hz, ArH), 7.92 (dm, 1H, ArH), 8.05 (d, 1H, J=9.5 Hz, ArH);

IR (CHCl₃, cm⁻¹): 3510, 3420 (NH₂), 1630, 1610 (aromatic C—C);

Ms (z/e): 255 (100%), 234 (79%), 212 (75%);

Anal. Calcd: C, 61.17; H, 4.74; N, 5.49%. Found: C, 61.38; H, 4.40; N, 5.40%.

Step (3) Preparation of 2-Fluoro-6-methoxy-1-methyl-5-(trifluoromethyl)naphthalene A 250 mL nalgene bottle with magnetic stir bar under an N₂ atmosphere was charged with HF-pyridine (70%-30% by weight) (75 mL) and cooled to −78° C. in a dry ice-isopropanol bath. When the HF-pyridine solution was frozen, a solution of the 6-amino-2-methoxy-5-methyl-1-trifluoromethylnaphthalene (10.07 g, 39.4 mmol) in pyridine (25 mL, previously dried over KOH) was added slowly. Again, when the solution was frozen, solid sodium nitrite (4.55 g, 1.67 eq) was added and the dry ice-isopropanol bath was removed. The reaction mixture was stirred at room temperature for 30 minutes (after 10 minutes the frozen solids had melted). The reaction mixture was then heated in a 65° C. oil bath for 2 hours. During the heating period a foamy precipitate had collected in the reaction vessel. The reaction mixture was cooled to room temperature and added to water (1 L). The aqueous phase was extracted with ether (3×300 mL). The combined ether extracts were washed with saturated aqueous NaCl (200 mL). Silica gel (40 mL) was added to the ether phase and the ether was removed. The silica absorbate was flash chromatographed (95:5 petroleum ether:ethyl acetate) to provide the white solid product (7.82 g, 77%), m.p. 97°–99° C.

NMR (CDCl₃, 200 MHz): δ 2.56 (d, 3H, J=2.2 Hz, CH₃), 3.99 (s, 3H, OCH₃), 7.28 (d, 1H, J=9.3 Hz, ArH), 7.34 (t, 1H, J=9.3 Hz, ArH), 8.04 (m, 1H, ArH), 8.13 (d, 1H, J=9.3 Hz, ArH);

IR (CHCl₃, cm⁻¹): 1615 (aromatic C—C);

MS (z/e): 258 (96%);

Anal. Calcd.: C, 60.47; H, 3.98%. Found: C, 60.28; H, 3.81%.

We claim:

1. A compound of formula (I)

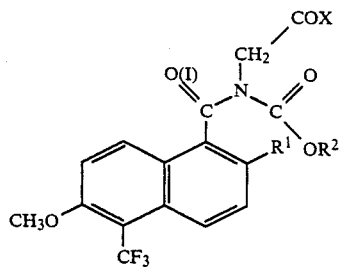

wherein R¹ is halogen or lower perfluoroalkoxy containing 1 to 3 carbon atoms; R² is lower alkyl containing 1 to 3 carbon atoms; X is —OH or —NH₂, or the pharmaceutically acceptable salt thereof, wherein X is —OH.

2. The compounds according to claim 1 wherein R¹ is fluorine, chlorine or bromine; R² is methyl or ethyl; X is —OH or —NH₂, or the pharmaceutically acceptable salt thereof, wherein X is —OH.

3. The compound according to claim 2 designated N-[[2-fluoro-6-methoxy-5-(trifluoromethyl)-1-naphthalenyl]carbonyl]-N-(methoxycarbonyl)glyine, or the pharmaceutically acceptable salt thereof.

4. The compound according to claim 2 designated [[[2-fluoro-6-methoxy-5-(trifluoromethyl)-1-naphthalenyl]carbonyl](methoxycarbonyl)amino]acetamide.

5. The compound according to claim 2 designated N-(ethoxycarbonyl)-N-[[2-fluoro-6-methoxy-5-(trifluoromethyl)-1-naphthalenyl]carbonyl]glycine, or the pharmaceutically acceptable salt thereof.

6. The compound according to claim 2 designated N-[[2-chloro-6-methoxy-5-(trifluoromethyl)-1-naphthalenyl]carbonyl]-N-(methoxycarbonyl)glycine, or the pharmaceutically acceptable salt thereof.

7. The compound according to claim 2 designated N-[[2-bromo-6-methoxy-5-(trifluoromethyl)-1-naphthalenyl]carbonyl]-N-(methoxycarbonyl)glycine, or the pharmaceutically acceptable salt thereof.

8. The compound of formula (VI)

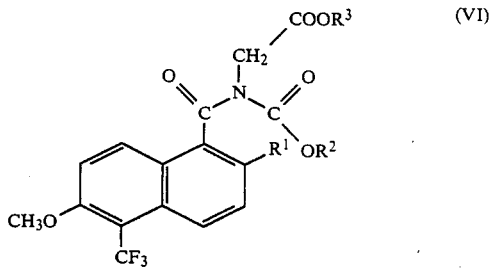

wherein R₁ is halogen or lower perfluoroalkoxy containing 1 to 3 carbon atoms; R² is lower alkyl containing 1 to 3 carbon atoms; and R³ is t-butyl or benzyl.

9. A pharmaceutical composition for preventing or relieving neuropathy, nephropathy, retinopathy, or cataracts in a diabetic mammal, which comprises an alleviating or prophylactic amount of a compound of claim 1 and a pharmaceutically acceptable carrier.

10. A method of preventing or relieving neuropathy, nephropathy, retinopathy, or cataracts in a diabetic mammal, which comprises administering to said mammal an alleviating or prophylactic amount of a compound of claim 1.

11. A method of preserving or relieving neuropathy, nephropathy, retinopathy, or cataracts in a diabetic mammal, which comprises administering to said mammal an alleviating or prophylactic amount of a compound of claim 1 in conjunction with insulin or an oral hypoglycemic agent.

* * * * *